(12) United States Patent
Peultier et al.

(10) Patent No.: US 11,490,933 B2
(45) Date of Patent: Nov. 8, 2022

(54) SURGICAL SYSTEM

(71) Applicant: Warsaw Orthopedic, Inc., Warsaw, IN (US)

(72) Inventors: Bertrand Peultier, Les Hopitaux Neufs (FR); Loic Josse, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 82 days.

(21) Appl. No.: 16/487,057

(22) PCT Filed: Feb. 17, 2017

(86) PCT No.: PCT/IB2017/000288
§ 371 (c)(1),
(2) Date: Aug. 19, 2019

(87) PCT Pub. No.: WO2018/150214
PCT Pub. Date: Aug. 23, 2018

(65) Prior Publication Data
US 2020/0054361 A1   Feb. 20, 2020

(51) Int. Cl.
*A61B 17/70* (2006.01)
*A61B 17/02* (2006.01)
(52) U.S. Cl.
CPC ........ *A61B 17/708* (2013.01); *A61B 17/7085* (2013.01); *A61B 2017/0256* (2013.01)
(58) Field of Classification Search
CPC ........................................ A61B 17/7077–708
See application file for complete search history.

(56) References Cited

U.S. PATENT DOCUMENTS

| | | | | |
|---|---|---|---|---|
| 9,480,504 | B1* | 11/2016 | Schafer | A61B 17/7083 |
| 9,907,582 | B1* | 3/2018 | Olea | A61B 17/60 |
| 2005/0245928 | A1* | 11/2005 | Colleran | A61B 17/708 606/90 |
| 2008/0077138 | A1* | 3/2008 | Cohen | A61B 17/708 606/86 A |

(Continued)

FOREIGN PATENT DOCUMENTS

| | | |
|---|---|---|
| CN | 102821673 A | 12/2012 |
| CN | 103690205 A | 4/2014 |

OTHER PUBLICATIONS

International Search Report for PCT date of completion is Nov. 2, 2017 (3 pages).

(Continued)

*Primary Examiner* — Eduardo C Robert
*Assistant Examiner* — Steven J Cotroneo
(74) *Attorney, Agent, or Firm* — Sorell, Lenna & Schmidt, LLP

(57) ABSTRACT

A surgical system includes a first implant support that is engageable with a receiver of a first fastener having a shaft fixed with vertebral tissue. At least one adaptor includes a first adaptor extending longitudinally along and being engageable with the first implant support. The first adaptor is oriented to releasably engage a surgical instrument to distract and/or compress the vertebral tissue. An angulation module is connected to at least one of the first adaptor, the first implant support and the surgical instrument. Surgical instruments, constructs, implants and methods are disclosed.

19 Claims, 22 Drawing Sheets

(56) References Cited

U.S. PATENT DOCUMENTS

| | | | |
|---|---|---|---|
| 2008/0077155 A1* | 3/2008 | Diederich | A61B 17/708 606/105 |
| 2008/0125788 A1* | 5/2008 | Cohen | A61B 17/708 606/104 |
| 2008/0154280 A1 | 6/2008 | Schumacher et al. | |
| 2012/0191143 A1* | 7/2012 | Nayet | A61B 17/708 606/86 A |
| 2014/0039567 A1 | 2/2014 | Hoefer et al. | |
| 2014/0228899 A1* | 8/2014 | Thoren | A61B 17/7077 606/86 R |
| 2015/0066088 A1* | 3/2015 | Brinkman | A61B 17/7077 606/264 |
| 2016/0022317 A1* | 1/2016 | Kraus | A61B 17/708 606/267 |
| 2016/0089188 A1* | 3/2016 | McBride, Jr. | A61B 17/7089 606/279 |
| 2018/0014862 A1* | 1/2018 | Raina | A61B 17/7007 |
| 2018/0153585 A1* | 6/2018 | Levine | A61B 17/1655 |
| 2018/0214189 A1* | 8/2018 | Olea | A61B 17/7077 |
| 2019/0090979 A1* | 3/2019 | Medeiros | A61F 2/30 |
| 2019/0110785 A1* | 4/2019 | Serokosz | A61B 17/7077 |
| 2019/0216453 A1* | 7/2019 | Predick | A61B 17/025 |
| 2020/0054362 A1* | 2/2020 | Peultier | A61B 17/7086 |
| 2020/0405359 A1* | 12/2020 | Hayes | A61B 17/7079 |

OTHER PUBLICATIONS

China National Intellectual Property Administration CNIPA, Notice of the First Office Action, Application/Patent No. 201780086030.0, dated Jul. 12, 2022.

* cited by examiner

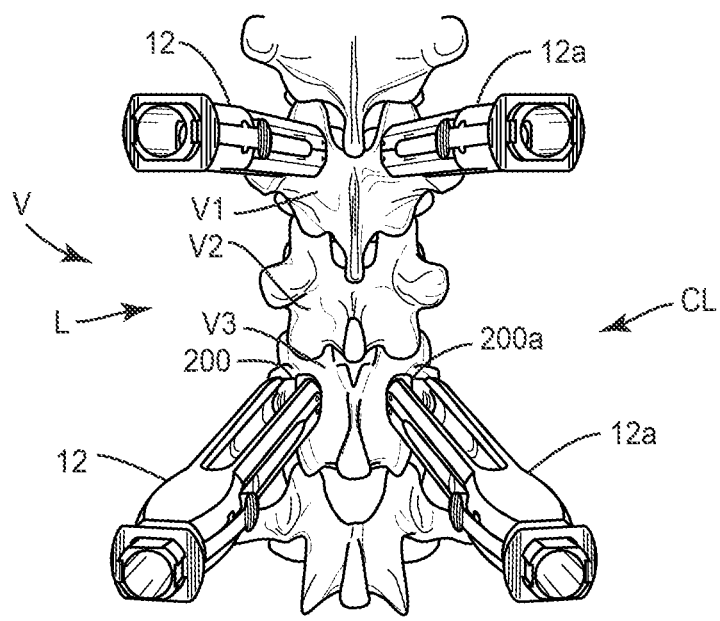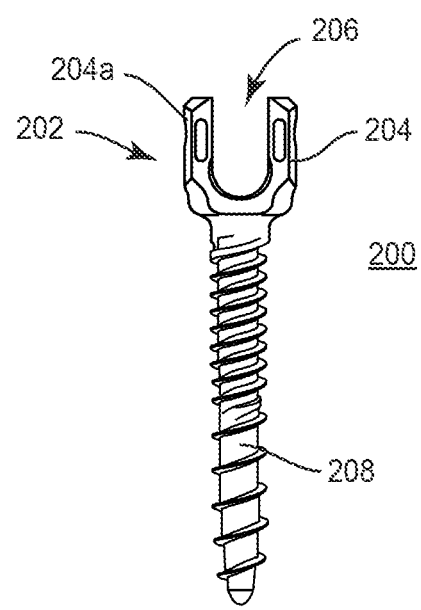
FIG. 5
FIG. 7
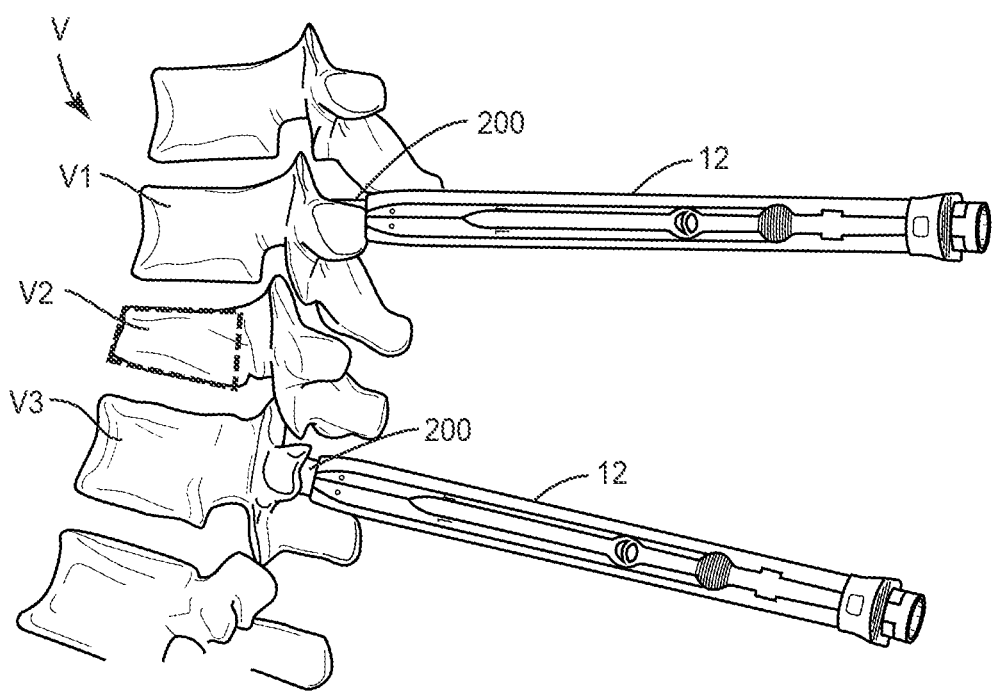
FIG. 6

SURGICAL SYSTEM

CROSS-REFERENCE TO RELATED APPLICATIONS

This application is a U.S. Application which claims benefit of and priority to Patent Cooperation Treaty Application Serial No. PCT/IB2017/000288 filed 17 Feb. 2017, the disclosure of the above-identified application is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical system is provided. The surgical system includes at least one implant support including a first implant support that is engageable with a receiver of a first fastener having a shaft fixed with vertebral tissue. At least one adaptor includes a first adaptor extending longitudinally along and being engageable with the first implant support. The first adaptor is oriented to releasably engage a surgical instrument to distract and/or compress the vertebral tissue. An angulation module is connected to at least one of the first adaptor, the first implant support and the surgical instrument. In some embodiments, surgical instruments, constructs, implants and methods are disclosed.

In one embodiment, a surgical adaptor is provided. The surgical adaptor includes an arm that includes a longitudinal member and a transverse member. The longitudinal member extends along and is engageable with an extender that is connected with a receiver of a fastener having a shaft fixed with vertebral tissue. The transverse member is disposed about the extender and defines a recess configured for disposal of a spinal rod. The longitudinal member is oriented to releasably engage a surgical instrument to manipulate the vertebral tissue.

In one embodiment, a surgical adaptor includes an expandable sleeve extending along and being engageable with an extender that is connected with a receiver of a fastener having a shaft fixed with vertebral tissue. An arm is connected with the sleeve adjacent the receiver and is oriented to releasably engage a surgical instrument to manipulate the vertebral tissue. The arm is rotatably adjustable to connect the extender with the surgical instrument.

BRIEF DESCRIPTION OF THE DRAWINGS

The present disclosure will become more readily apparent from the specific description accompanied by the following drawings, in which:

FIG. 5 is a plan view of components of one embodiment of a surgical system in accordance with the principles of the present disclosure disposed with vertebrae;

FIG. 6 is a side view of components of one embodiment of a surgical system in accordance with the principles of the present disclosure disposed with vertebrae;

FIG. 7 is a side view of components of one embodiment of a surgical system in accordance with the principles of the present disclosure;

DETAILED DESCRIPTION

Figure 1:
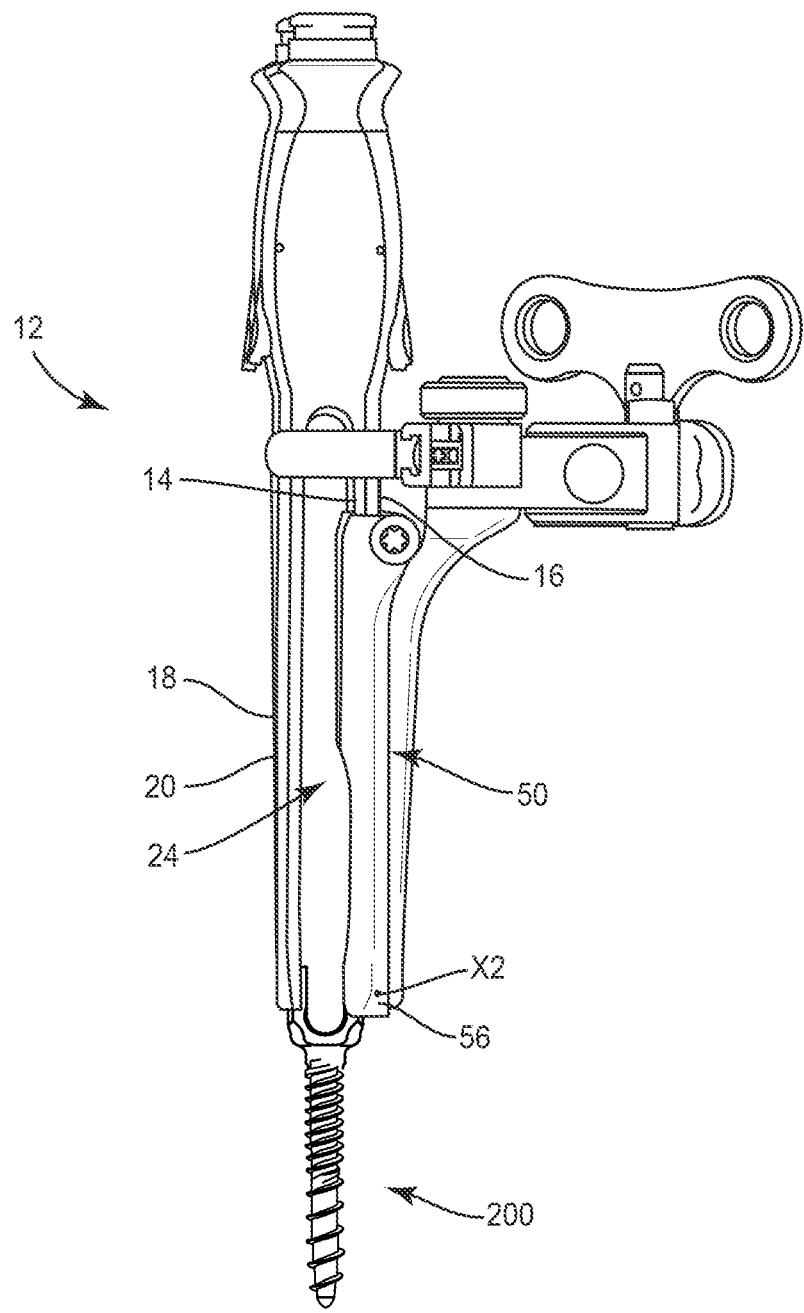
FIG. 1 is a side view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes surgical instruments that allow vertebral manipulation to treat spinal disorders, as described herein, for managing lordosis and/or kyphosis restoration. In some embodiments, the surgical instruments allow for parallel distraction and/or compression of vertebral tissue.

In some embodiments, the present surgical system includes a trauma instrument. In some embodiments, the present surgical system is utilized with a method to correct complex spinal deformities. In some embodiments, the present surgical system is utilized with a method to treat degenerative spinal disorders and/or employed with transforaminal lumbar interbody fusion procedures. In some embodiments, the present surgical system is configured for utilization with a sagittal adjusting screw (SAS), a fixed axis screw (FAS) and/or a multi-axial screw (MAS). In some embodiments, the present surgical system comprises a plurality of distractors, such as, for example, two distractors disposed along a side of vertebrae to perform a ligamentotaxy procedure. In some embodiments, the present surgical system comprises a single distractor to treat degenerative spinal disorders, for example, for disposal along a side of vertebrae oriented for decompression and/or interbody cage insertion.

In some embodiments, the present surgical system includes a percutaneous surgical system for use in a ligamentotaxy of a traumatic thoracic lumbar spine. In some embodiments, the present surgical system includes a surgical system that allows restoration of an angle during ligamentotaxy at a level of an implant, such as, for example, a head of a screw disposed at a surgical site to facilitate a more precise reduction of the trauma. As such, an extender connected with the screw head can include a point of rotation at the screw head level. In some embodiments, the present surgical system includes a micrometric distractor and/or compressor to facilitate angle reduction. In some embodiments, the present surgical system provides for free hand base angle reduction and an increased reduction sensation. In some embodiments, the present surgical system provides up to 36 angular degrees of lordosis and/or kyphosis restoration.

In some embodiments, the present surgical system includes a surgical instrument connected with an adaptor, which is utilized with a FAS. In some embodiments, the present surgical system includes an adaptor having a percutaneous arm. In some embodiments, the adaptor includes an outer sleeve configured for connection with an implant support, such as, for example, an extender. In some embodiments, the adaptor is connected with the extender for insertion of an implant, such as for example, a spinal rod. In some embodiments, the adaptor includes a pivot hinge that connects the outer sleeve with the arm. In some embodiments, the surgical system includes an angulation module configured for connection with the adaptor and including arms for connection with the extender. In some embodiments, the angulation module is configured for individual angulation of the extenders in a range of +/−20 degrees. In some embodiments, a compressor/distractor is utilized for parallel distraction. In some embodiments, the surgical instrument includes a compressor/distractor having a reversible ratchet with a neutral, freely moveable position. In some embodiments, the present surgical system is employed with a procedure for implantation of a FAS percutaneously.

In some embodiments, the adaptor is employed with a surgical method including the step of inserting the adaptor with a surgical site and the step of sliding a sleeve along the extender. In some embodiments, the method includes the step of securing the sleeve to the extender. In some embodiments, the method includes the step of connecting a compressor/distractor with the adaptor. In some embodiments, the method includes the step of connecting an angulation module with the adaptor, the compressor/distractor and the extender. In some embodiments, the method includes the step of securing the angulation module, the compressor/distractor and the adaptor with a locking element. In some embodiments, the method includes the step of distracting and/or compressing a posterior ligament. In some embodiments, the method includes the step of actuating a rack and pinion mechanism disposed with the compressor/distractor to facilitate distraction or compression. In some embodiments, the method includes the step of correcting a vertebral angle with the angulation module. In some embodiments, the method includes the step of manually correcting vertebrae using the angulation module to manipulate the extenders, for example, by pivoting the extenders. In some embodiments, the method includes the step of utilizing the angulation module to maintain or fix a corrected vertebrae angle, relative to a compressor/distractor, during compression or distraction with the compressor/distractor.

In some embodiments, the present surgical system includes a surgical instrument connected with an adaptor, which are utilized with a SAS. In some embodiments, the present surgical system is employed with a surgical technique for the implantation of spinal implants, such as, for example, spinal rods and setscrews. In some embodiments, the spinal rods and setscrews are implanted percutaneously. In some embodiments, the spinal rods are reduced relative to a screw head. In some embodiments, the present surgical system is employed with a surgical technique for release of screw head mobility. In some embodiments, the present surgical system is employed with a surgical technique for release of pressure applied during spinal rod reduction. In some embodiments, the present surgical system is employed with a surgical technique for distraction of a posterior ligament. In some embodiments, the surgical system includes manual winglets or a T25 driver that engages a compressor/distractor for performing compression or distraction of vertebrae.

In some embodiments, the present surgical system includes a surgical instrument configured to compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, degenerative kyphosis. In some embodiments, the present surgical system is employed to treat hyper-kyphosis, flat lumbar back, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-4A, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with spinal constructs attached with vertebrae to manipulate tissue and/or correct a spinal disorder, such as, for example, a sagittal deformity, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Figure 4:
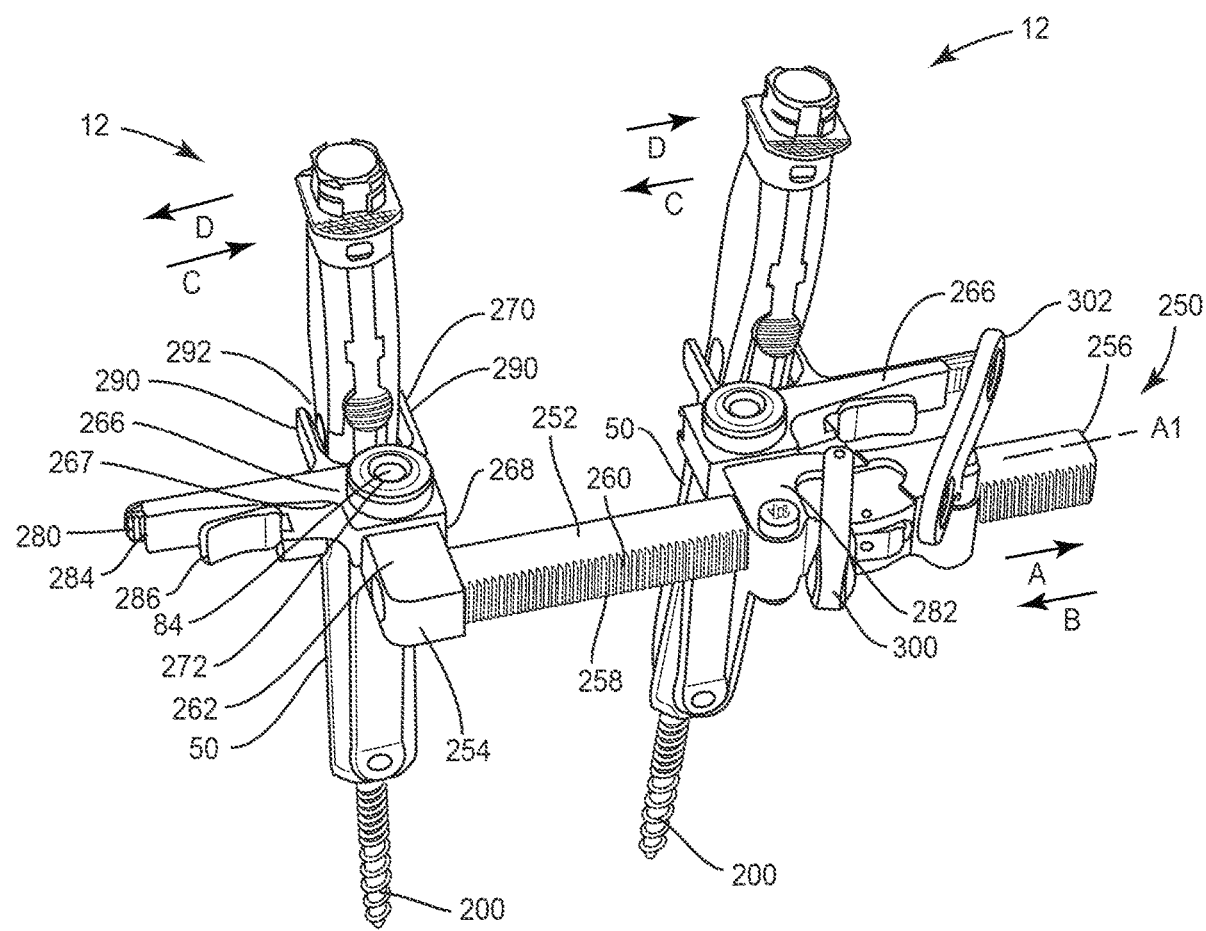
FIG. 4 is a perspective view of components of one embodiment of a surgical system in accordance with the principles of the present disclosure.

Surgical system 10 includes implant supports, such as, for example, extenders 12. Extenders 12 are engageable with bone fasteners, such as, for example, a FAS 200 and a surgical instrument, such as, for example, a compressor/distractor 250 to manipulate tissue, as shown in FIGS. 4-6 and described herein. Extender 12 includes members, such as, for example, legs 14, 18. Leg 14 includes a surface 16 and leg 18 includes a surface 20.

Legs 14, 18 are configured for translation over a portion of FAS 200 and engagement with an adaptor 50, as described herein. Legs 14, 18 are disposed in spaced apart relation and define a slot 24 configured for disposal of an implant, such as, for example, a spinal rod 210. Legs 14, 18 are relatively movable to capture FAS 200. In some embodiments, extenders 12 are manipulable, as described herein, to provide counter-torque for small deformity maneuvers and manipulation of vertebrae during a surgical treatment, for example, to displace, pull, twist or align vertebrae.

Figure 2:
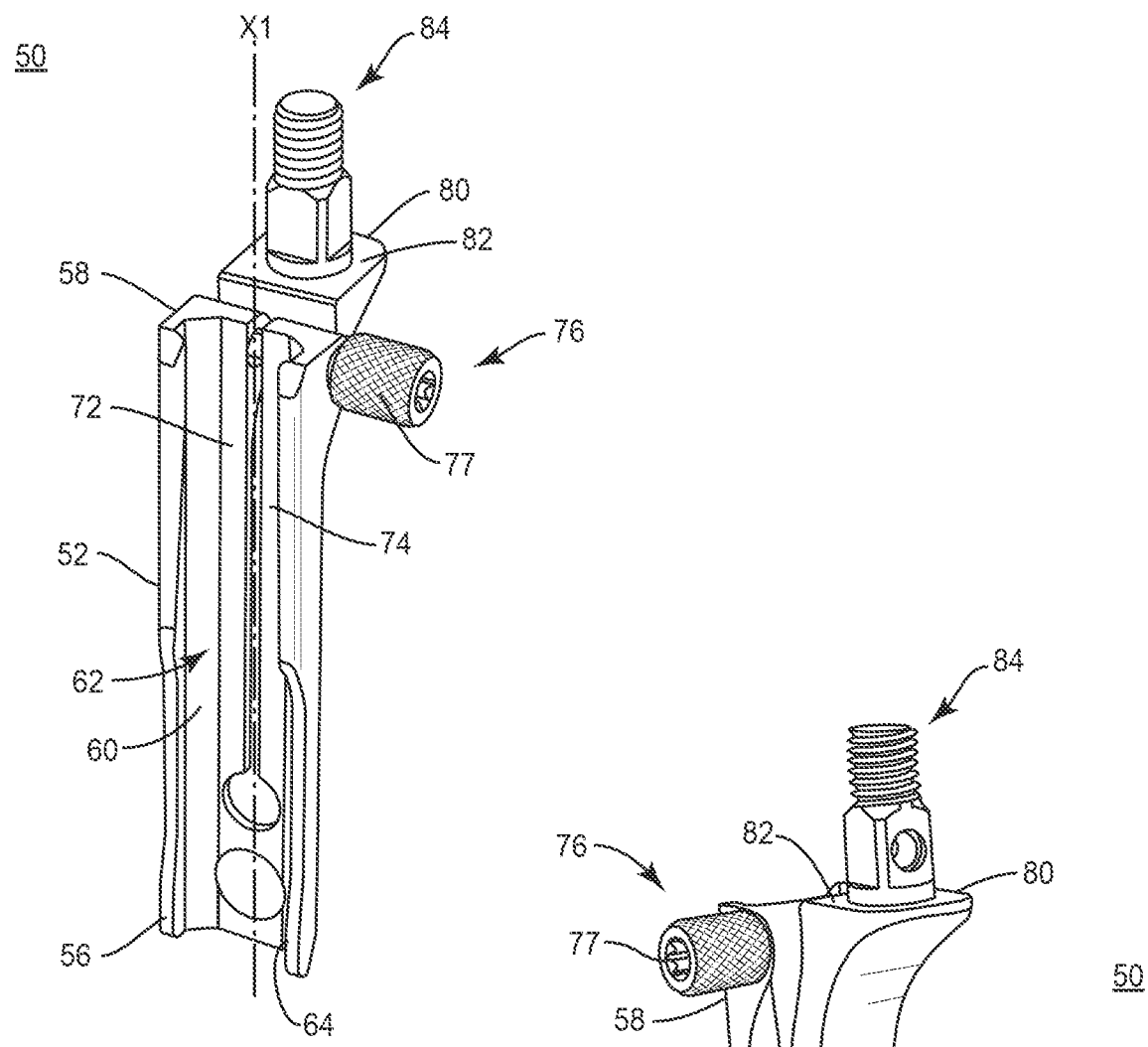
FIG. 2 is a perspective view of components of one embodiment of a surgical system in accordance with the principles of the present disclosure.
Figure 3:
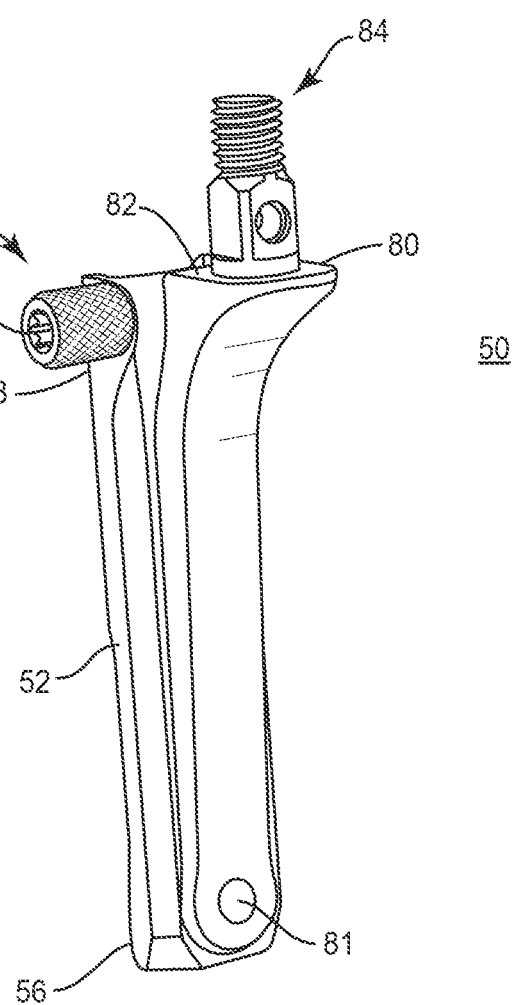
FIG. 3 is a perspective view of components of one embodiment of a surgical system in accordance with the principles of the present disclosure.

Adaptor 50 includes a body, such as, for example, a sleeve 52. Sleeve 52 extends along an axis X1 between an end 56 and an end 58, as shown in FIGS. 2 and 3. Sleeve 52 includes a surface 60 that defines a channel 62. Channel 62 is configured for disposal of legs 14, 18. Sleeve 52 is configured to extend longitudinally along legs 14, 18. End 56 includes a capture portion 64.

Sleeve 52 includes an extension 72 and an extension 74, which are relatively movable. Extensions 72, 74 are connected by an actuator 76 disposed at end 58. Actuator 76 includes a knob 77 that is rotatable to draw and/or pull extensions 72, 74 to compress and capture legs 14, 18. Extensions 72, 74 apply a force to surfaces 16, 20 to fix adaptor 50 with extenders 12. In some embodiments, extensions 72, 74 are resiliently biased to an open configuration and actuation of knob 77 overcomes the bias of extensions 72, 74 to a closed configuration to capture legs 14, 18 with extensions 72, 74.

End 58 includes an arm 80 extending therefrom, which extends axially along axis X1. In some embodiments, arm 80 is may be variously oriented relative to axis X1, such as, for example, perpendicular, angular and/or offset. Arm 80 is connected to sleeve 52 by a pin hinge 81. Pin hinge 81 facilitates rotation of arm 80 relative to sleeve 52 and/or FAS 200. Rotation of arm 80 facilitates connection of adaptor 50 and extenders 12 with compressor/distractor 250, as described herein. Arm 80 includes a surface 82 that defines a threaded lock surface 84. Surface 84 is engageable with a lock nut 274 to fix compressor/distractor 250 and an angulation module 266 with extenders 12 and adaptors 50, as described herein. In some embodiments, surface 84 may have alternative locking and/or tool engaging surfaces, such as, for example, rectangular, polygonal, hexalobe, oval, irregular, cruciform, phillips, square, polygonal or star cross sectional configuration.

Figure 3A:
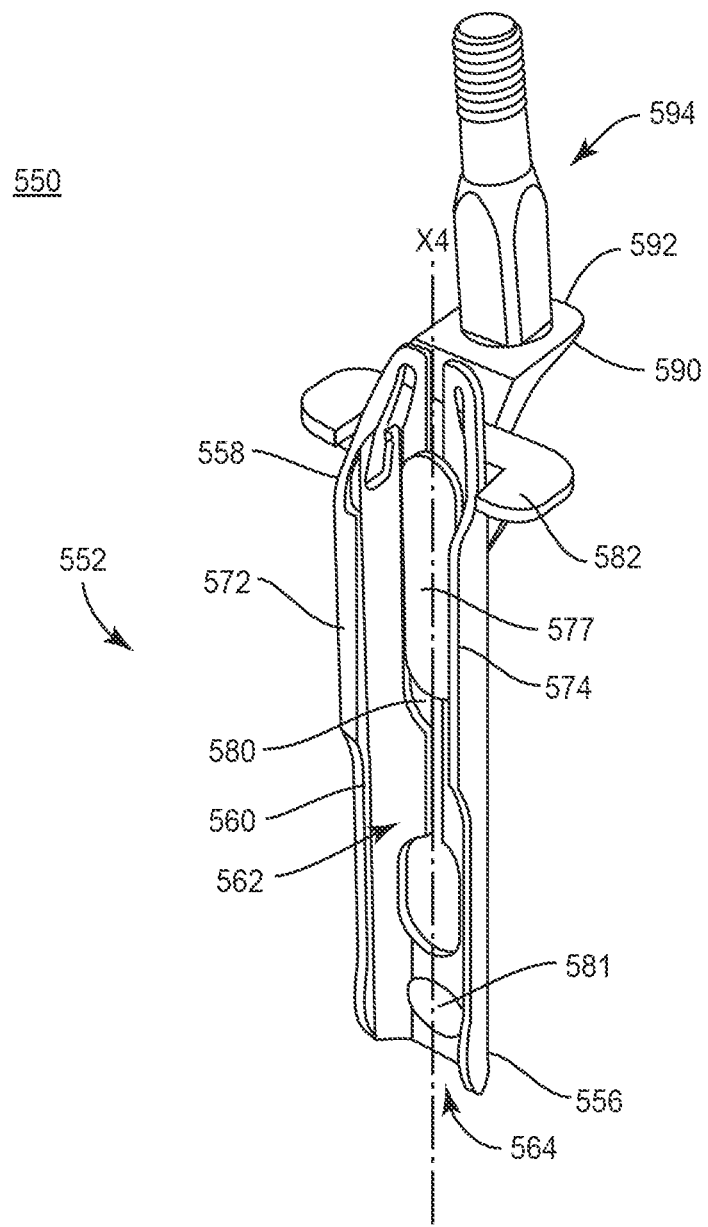
FIG. 3A is a perspective view of components of one embodiment of a surgical system in accordance with the principles of the present disclosure.

In one embodiment, as shown in FIG. 3A, surgical system 10 includes an adaptor 550, similar to adaptor 50 described herein. Legs 14, 18 are engageable with adaptor 550, which includes a body, such as, for example, a sleeve 552. Sleeve 552 extends along an axis X4 between an end 556 and an end 558. Sleeve 552 includes a surface 560 that defines a channel 562. Channel 562 is configured for disposal of legs 14, 18. Sleeve 552 is configured to extend longitudinally along legs 14, 18. End 556 includes a capture portion 564.

Sleeve 552 includes an extension 572 and an extension 574, which are relatively movable. Extensions 572, 574 are resiliently biased and expandable to an open configuration. Extensions 572, 574 define a longitudinal slot 580 for slidable disposal of a slider 577 between extensions 572, 574. Slider 577 is translatable relative to extensions 572, 574 along slot 580. Slider 577 includes a tab 582 that defines a cavity configured for disposal of sleeve 552.

Slider 577 travels along slot 580 and tab 582 is translatable relative to sleeve 552, for example, in a downward direction along the sides of extensions 572, 574, to engage and dispose extensions 572, 574 in a closed configuration such that tab 582 engages extensions 572, 574 to overcome the bias of extensions 572, 574. In the closed configuration, extensions 572, 574 apply a force to surfaces 16, 20 to capture legs 14, 18 and fix adaptor 550 with extenders 12. Tab 582 is translatable relative to sleeve 552, for example, in an upward direction along the sides of extensions 572, 574, to release from and dispose extensions 572, 574 in an open configuration. In the open configuration, extensions 572, 574 are resiliently biased to expand such that extensions 572, 574 can receive legs 14, 18.

End 558 includes an arm 590 extending therefrom, which extends axially along axis X4. In some embodiments, arm 590 may be variously oriented relative to axis X4, such as, for example, perpendicular, angular and/or offset. Arm 590 is connected to sleeve 552 by a pin hinge 581. Pin hinge 581 facilitates rotation of arm 590 relative to sleeve 552 and/or FAS 200. Rotation of arm 590 facilitates connection of adaptor 550 and extenders 12 with compressor/distractor 250, as described herein. Arm 590 includes a surface 592 that defines a threaded lock surface 594, similar to surface 84 described herein. Surface 594 is engageable with lock nut 274 to fix compressor/distractor 250 and angulation module 266 with extenders 12 and adaptors 550, as described herein.

Figure 19:
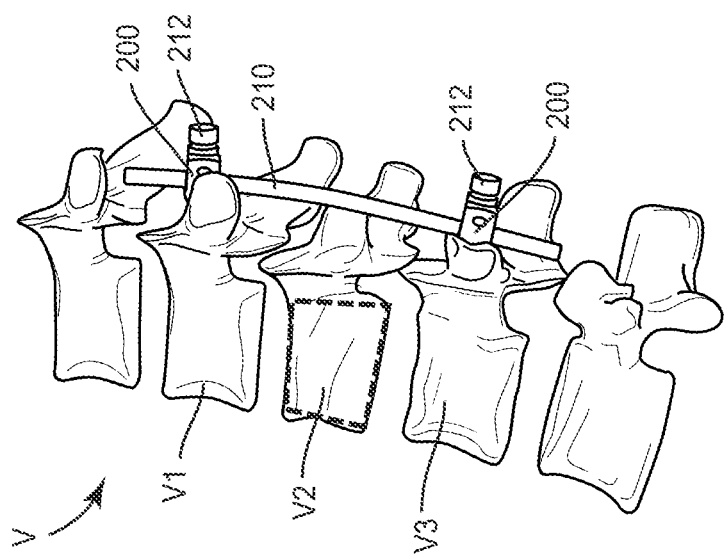
FIG. 19 is a side view of components of one embodiment of a surgical system in accordance with the principles of the present disclosure disposed with vertebrae.

FAS 200 includes a receiver 202 having a pair of spaced apart arms 204, 204a, as shown in FIG. 7. Receiver 202 is configured for engagement with extenders 12, as described herein. Arms 204, 204a include an inner surface that defines a U-shaped passageway 206 for disposal of rod 210, as described herein. The inner surface of receiver 202 includes a thread form configured for engagement with a set screw 212 (FIG. 19). Set screw 212 is threaded with receiver 202 to attach, fix and/or connect rod 210 with FAS 200 including a shaft 208 attached with tissue to facilitate connection of the tissue with surgical instruments for a correction treatment, as described herein.

Compressor/distractor 250 includes a longitudinal element, such as, for example, a rack 252, as shown in FIG. 4. Rack 252 extends between an end 254 and an end 256 defining a longitudinal axis A1. Rack 252 is configured to connect adjacent extenders 12. Rack 252 includes an outer surface 258 having a plurality of teeth, such as, for example, splines 260 engageable with an arm 282, as described herein. Rack 252 includes an arm 262 extending from end 254. In some embodiments, arm 262 is attached with rack 252 with, for example, with clips, hooks, adhesives and/or flanges.

Arm 262 includes a surface that defines an opening (not shown) configured for disposal of surface 84 for mounting compressor/distractor 250 with extender 12, angulation module 266 and adaptor 50 or adaptor 550. Rack 252 includes arm 282 that is axially translatable along axis A1 relative to arm 262. Arm 282 includes a surface that defines an opening (not shown) configured for disposal of surface 84 for mounting compressor/distractor 250 with extender 12, angulation module 266 and adaptor 50 or adaptor 550.

Compressor/distractor 250 includes a ratchet, which includes splines 260 and arm 282 engageable in a bi-directional and/or two-way ratchet configuration. Arm 282 includes a latch 300 that includes a pinion or pawl (not shown) engageable with splines 260. Latch 300 is pivotable relative to arm 282 for disposal in a distraction position, as shown in FIG. 4. In the distraction position, latch 300 engages rack 252 to allow axial and/or incremental translation of arm 282 relative to arm 262/rack 252, in the direction shown by arrow A, and prevents axial translation of arm 282 relative to arm 262/rack 252, in an opposing direction as shown by arrow B. As such, distraction of vertebral tissue connected with extenders 12 can be performed.

Latch 300 is pivotable relative to arm 282 for disposal in a neutral position (not shown). In the neutral position, latch 300 disengages from rack 252 to allow free axial translation of arm 262/rack 252 relative to arm 282. Latch 300 is pivotable relative to arm 282 for disposal in a compression position (not shown). In the compression position, latch 300 engages rack 252 to allow axial and/or incremental translation of arm 282 relative to arm 262/rack 252, in the direction shown by arrow B, and prevents axial translation of arm 282 relative to arm 262/rack 252, in an opposing direction as shown by arrow A. As such, compression of vertebral tissue connected with extenders 12 can be performed. In some embodiments, a rotatable key 302 includes a gear surface engageable with splines 260 to axially and/or incrementally translate rack 252 to facilitate distraction and/or compression, as described herein.

Angulation modules 266 are connectable with compressor/distractor 250, extenders 12, adaptor 50 or adaptor 550, as shown in FIG. 4. Module 266 includes a surface that defines an opening 272 configured for disposal of surface 84 for mounting module 266 with compressor/distractor 250, extenders 12 and adaptor 50 or adaptor 550. Module 266 includes a body 267 that extends between an end 268 and an end 270. Module 266 includes a longitudinal element, such as, for example, a rack 280, as shown in FIG. 4. Rack 280 includes an outer surface having a plurality of teeth, such as, for example, splines 284.

Rack 280 includes spaced apart arms 290 that define a cavity 292. Arms 290 are configured for capture of extenders 12. Modules 266 are fixed with extenders 12 to allow for angulation and/or correction of vertebral tissue connected with extenders 12, individually, in combination or simultaneously. In some embodiments, engagement of extenders 12 with module 266 facilitates manipulation of vertebrae attached with extenders 12 through an angular range of 0 through 20 degrees of correction and/or relative to an initial orientation of vertebrae.

Body 267 includes a ratchet, which includes splines 284 and a latch 286 engageable in a uni-directional and/or one-way ratchet configuration. Latch 286 includes a pinion or pawl (not shown) engageable with splines 284. Latch 286 is disposable in a lordosis position, as shown in FIG. 4. In the lordosis position, latch 286 engages rack 280 to allow axial and/or incremental translation of rack 280 relative to body 267, in the direction shown by arrows C, and prevents axial translation of rack 280 relative to body 267, in an opposing direction as shown by arrows D. As such, angulation of vertebral tissue connected with extenders 12 to achieve lordosis can be performed. Latch 286 is engageable for disposal in a neutral position such that latch 286 disengages from rack 280 to allow free axial translation of body 267 relative to rack 280.

Figure 4A:
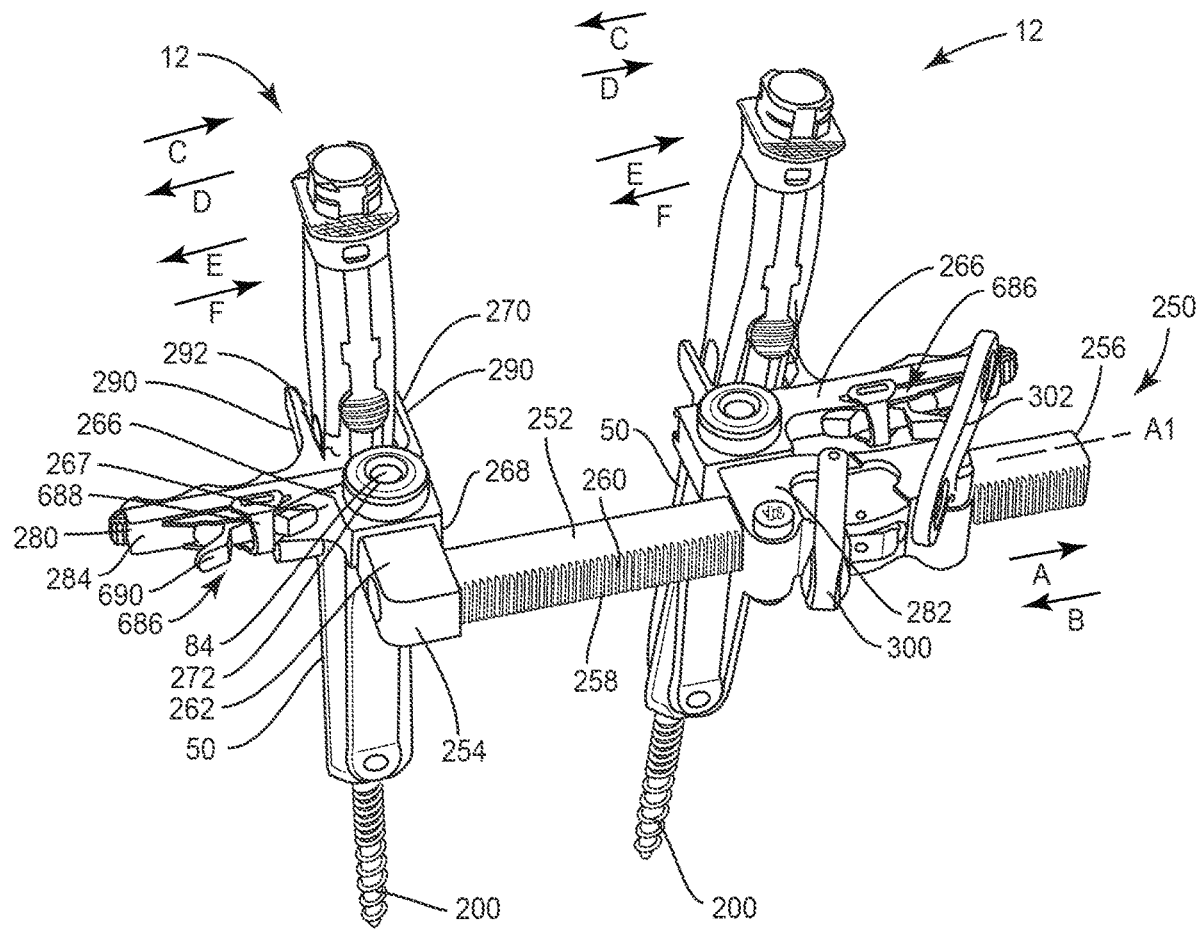
FIG. 4A is a perspective view of components of one embodiment of a surgical system in accordance with the principles of the present disclosure.
Figure 8:
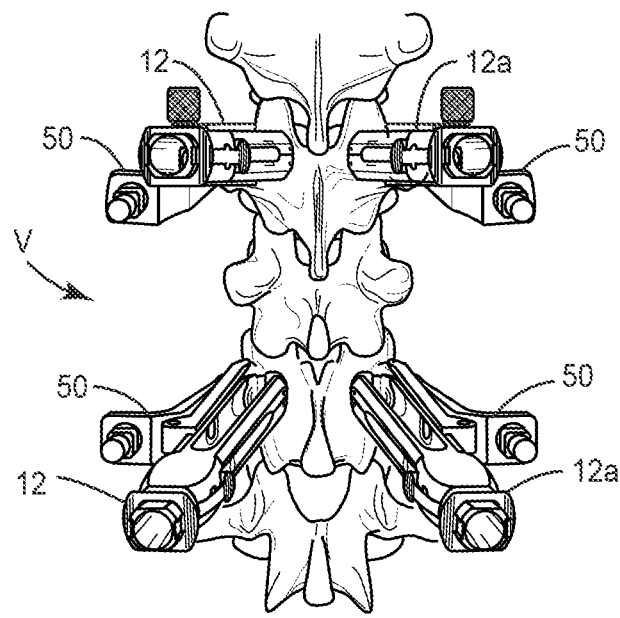
FIG. 8 is a plan view of components of one embodiment of a surgical system in accordance with the principles of the present disclosure disposed with vertebrae.
Figure 9:
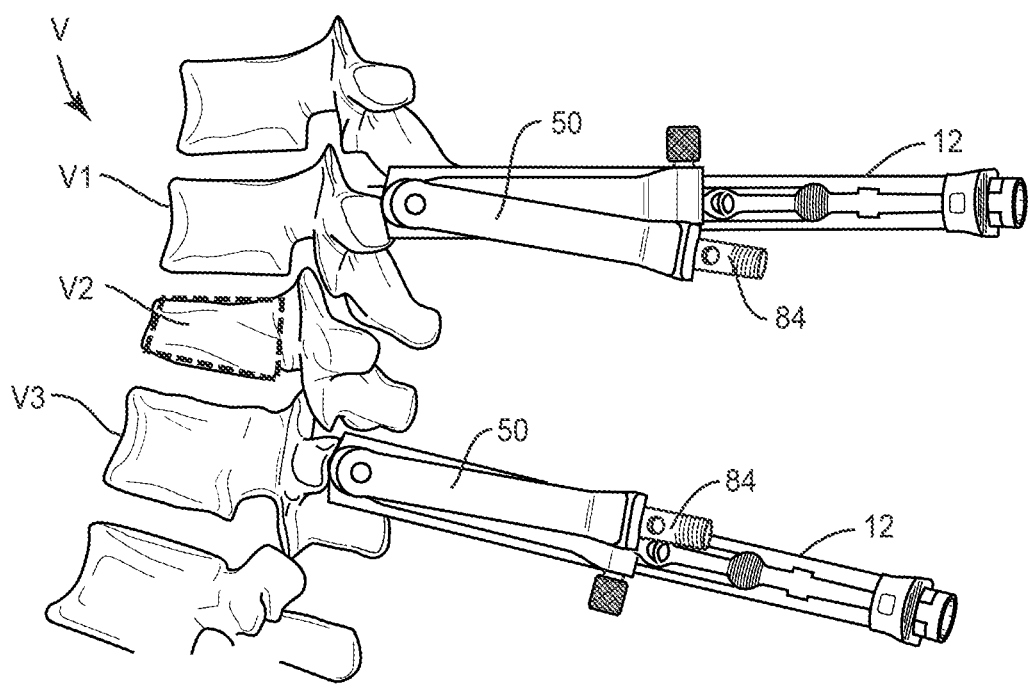
FIG. 9 is a side view of components of one embodiment of a surgical system in accordance with the principles of the present disclosure disposed with vertebrae.
Figure 10:
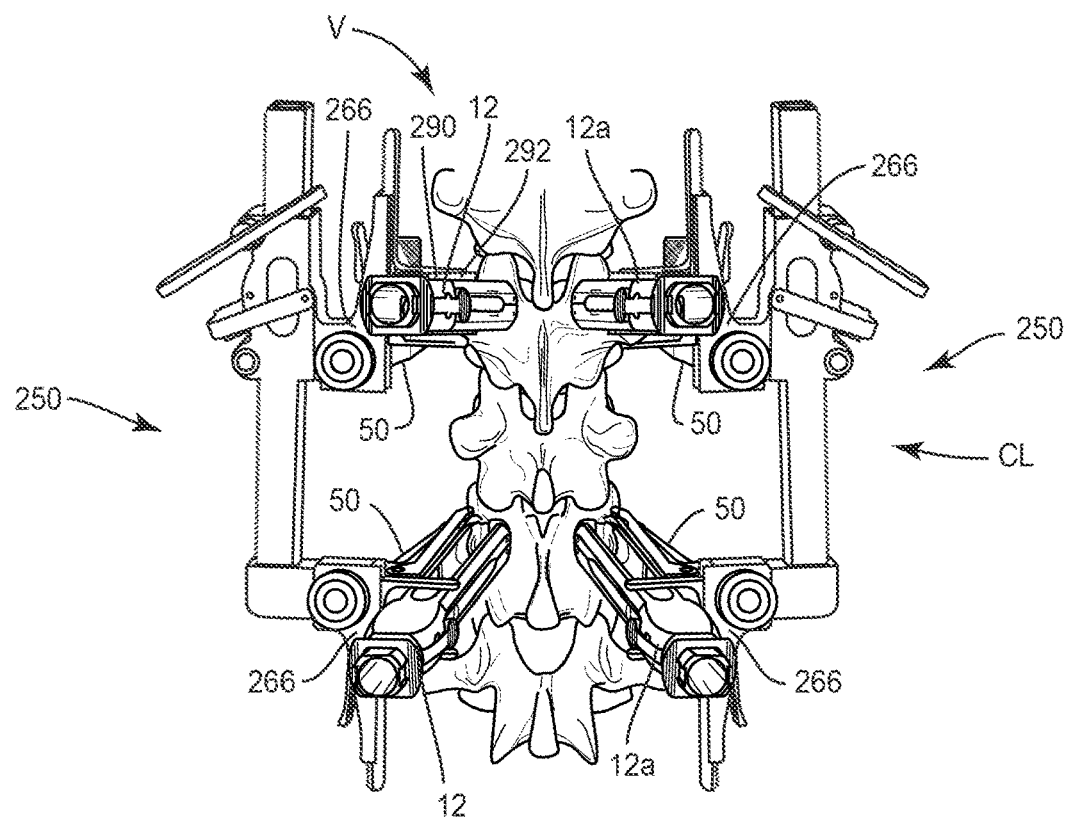
FIG. 10 is a plan view of components of one embodiment of a surgical system in accordance with the principles of the present disclosure disposed with vertebrae.

In one embodiment, as shown in FIG. 4A, body 267 includes a ratchet, which includes splines 284 and a latch 686 engageable in a bi-directional and/or two-way ratchet configuration. Latch 686 includes a slider 688 and a lever 690 having a pinion or pawl (not shown) engageable with splines 284. Slider 688 engages lever 690, which is pivotable relative to body 267 for disposal in a lordosis position, as shown in FIG. 4A. In the lordosis position, the pawl of lever 690 engages rack 280 in an orientation to allow axial and/or incremental translation of rack 280 relative to body 267, in the direction shown by arrows C, and prevents axial translation of rack 280 relative to body 267, in an opposing direction as shown by arrows D. As such, angulation of vertebral tissue connected with extenders 12 to achieve lordosis can be performed.

Slider 688 is engageable with lever 690, which is pivotable relative to body 267 in an opposing orientation for disposal in a kyphosis position. In the kyphosis position, the pawl of lever 690 engages rack 280 in an orientation to allow axial and/or incremental translation of rack 280 relative to body 267, in the direction shown by arrows E, and prevents axial translation of rack 280 relative to body 267, in an opposing direction as shown by arrows F. As such, angulation of vertebral tissue connected with extenders 12 to achieve kyphosis can be performed.

In some embodiments, connection of module 266 with adaptor 50 or adaptor 550 and extenders 12 facilitates correction of a vertebral angle of vertebrae, for example, to achieve a selected lordosis and/or kyphosis, via manipulation of modules 266, as described herein. In some embodiments, modules 266 are manipulated to manually correct a vertebral angle of vertebrae by pivoting extenders 12. In some embodiments, modules 266 are connected with adaptor 50 or adaptor 550, compressor/distractor 250 and/or extenders 12 to maintain a corrected vertebral angle of vertebrae during distraction and/or compression, as described herein.

In assembly, operation and use, surgical system 10, similar to the systems and methods described herein, is employed with a surgical procedure, for treatment of a spine of a patient including vertebrae V, as shown in FIGS. 5-20. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 18:
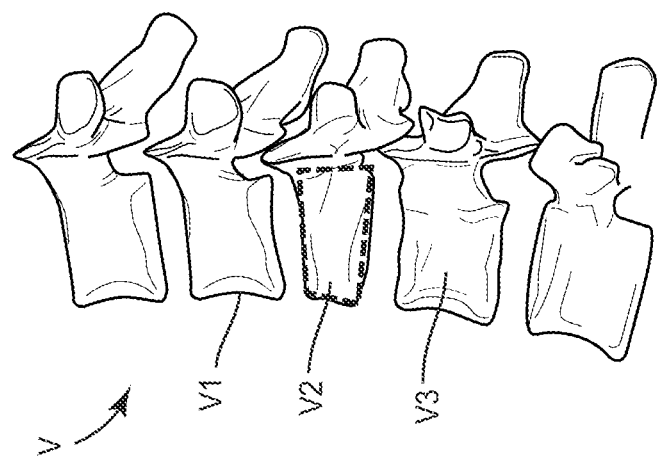
FIG. 18 is a side view of vertebrae.

Surgical system 10 is employed with a procedure for treatment of an applicable condition or injury of an affected section of a spinal column and adjacent areas within a body. For example, vertebrae V includes a vertebral level V1, a vertebral level V2 and a vertebral level V3, as shown in FIG. 18. Diseased and/or damaged vertebrae and intervertebral discs are disposed at vertebra V2 between vertebrae V1 and V3. In some embodiments, components of surgical system 10 are configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for implantation of components of surgical system 10. A preparation instrument (not shown) can be employed to prepare tissue surfaces of vertebrae V, as well as for aspiration and irrigation of a surgical region.

Pilot holes or the like are made in selected vertebrae V1 and V3 for receiving FAS 200, 200a. A driver (not shown) is disposed adjacent vertebrae V at a surgical site and is manipulated to drive, torque, insert or otherwise connect bone FAS 200, 200a with vertebrae V1 and V3. FAS 200, 200a are engaged with vertebrae V along a lateral side L and a contra-lateral side CL of vertebrae V, as shown in FIG. 5. Extenders 12 are engaged with FAS 200 and extenders 12a, 12a are engaged with FAS 200a.

Figure 11:
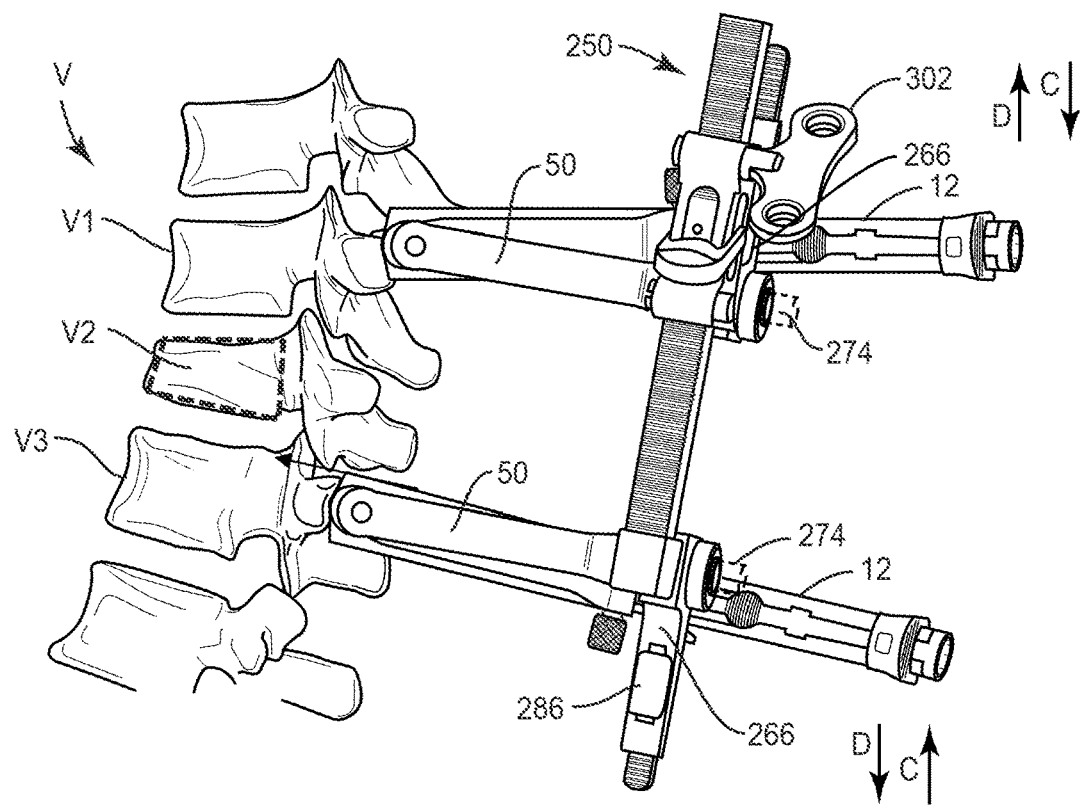
FIG. 11 is a side view of components of one embodiment of a surgical system in accordance with the principles of the present disclosure disposed with vertebrae.
Figure 12:
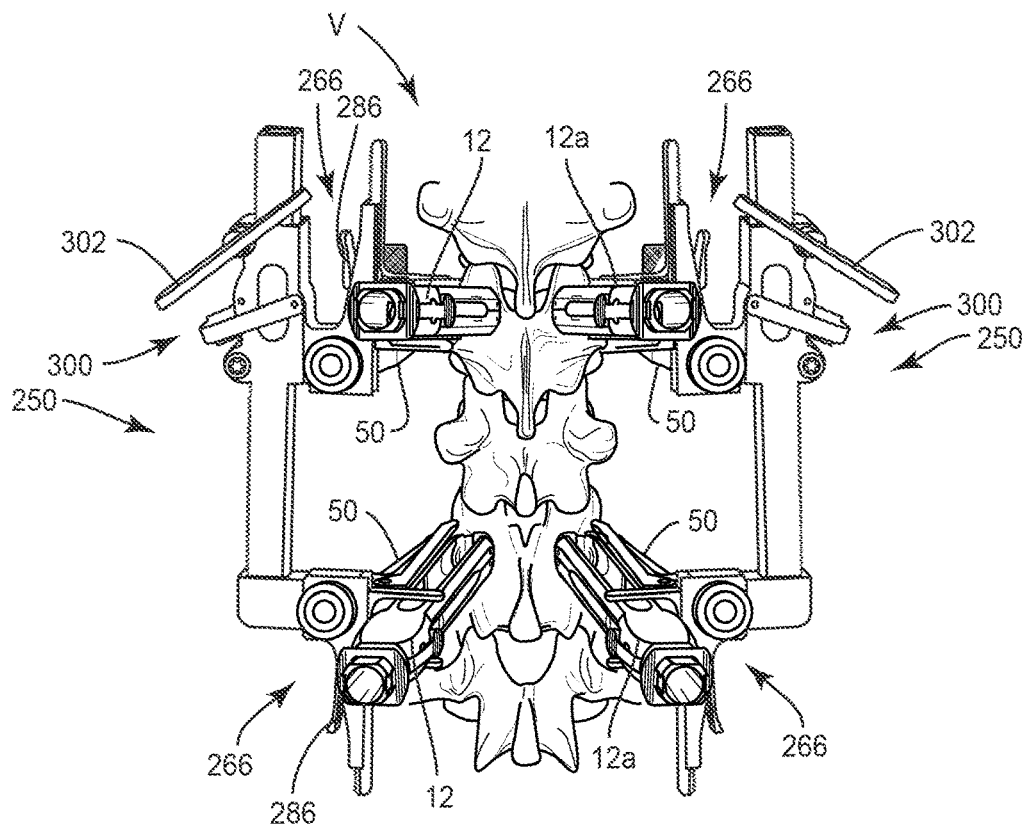
FIG. 12 is a plan view of components of one embodiment of a surgical system in accordance with the principles of the present disclosure disposed with vertebrae.

Adaptors 50 are connected with extenders 12, 12a, as described herein. Compressor/distractor 250 and modules 266 are mounted with adaptors 50 via surface 84 and lock nut 274 for fixation therewith, as described herein. Arms 290 of modules 266 capture extenders 12, 12a, as described herein. Modules 266 are fixed with extenders 12, 12a to allow for angulation and/or correction of vertebrae V connected with extenders 12, 12a. For example, latch 286 of module 266 is disposable in a lordosis position, as described herein, to allow translation of rack 280, in the direction shown by arrows C, and prevent translation of rack 280, in the direction shown by arrows D, relative to body 267, as shown in FIG. 11. As such, angulation of vertebrae V1, V3 connected with extenders 12, 12a to achieve a selected lordosis can be performed. Module 266 prevents translation of rack 280, in the direction shown by arrow D, relative to body 267 to maintain the selected lordosis during distraction and/or compression, as described herein.

Figure 13:
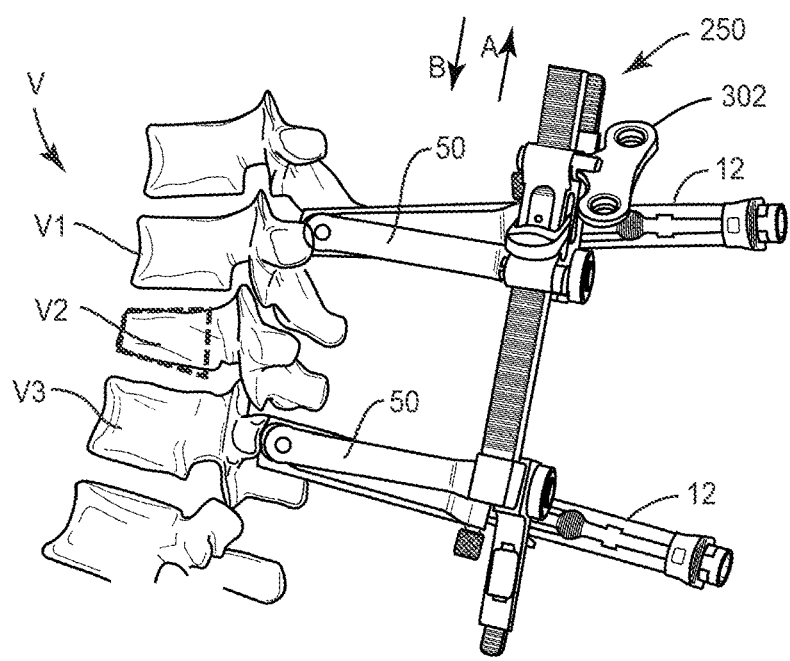
FIG. 13 is a side view of components of one embodiment of a surgical system in accordance with the principles of the present disclosure disposed with vertebrae.
Figure 14:
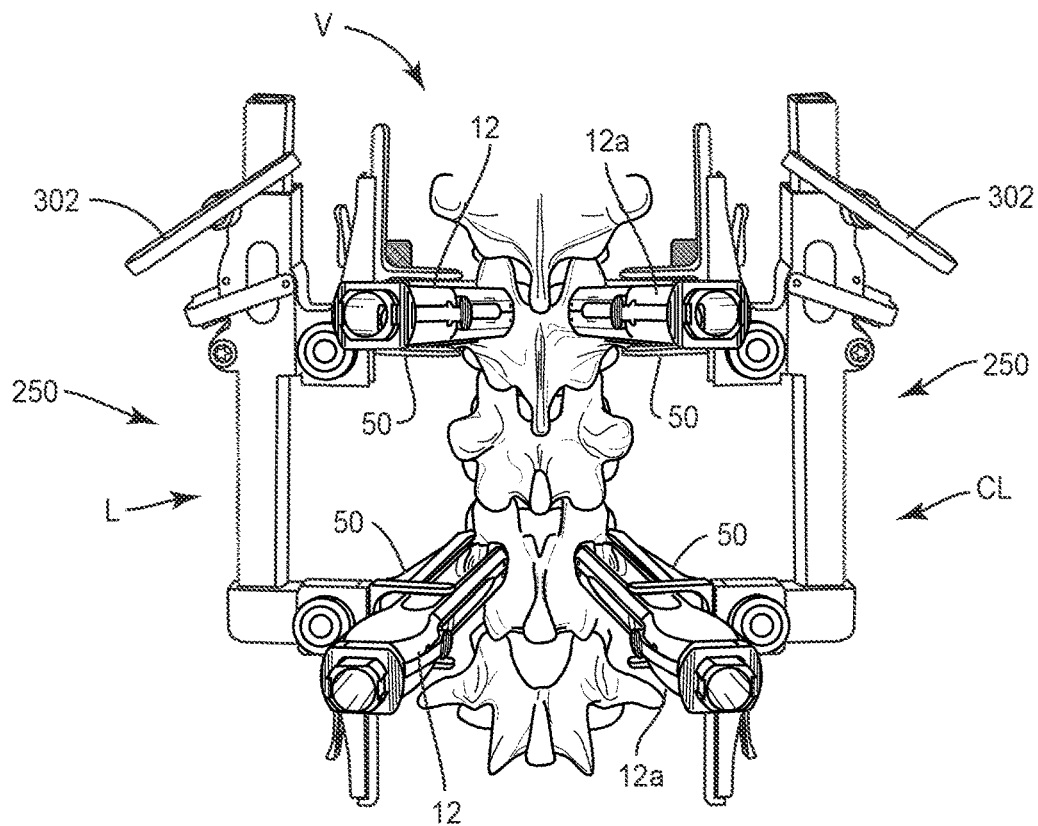
FIG. 14 is a plan view of components of one embodiment of a surgical system in accordance with the principles of the present disclosure disposed with vertebrae.
Figure 15:
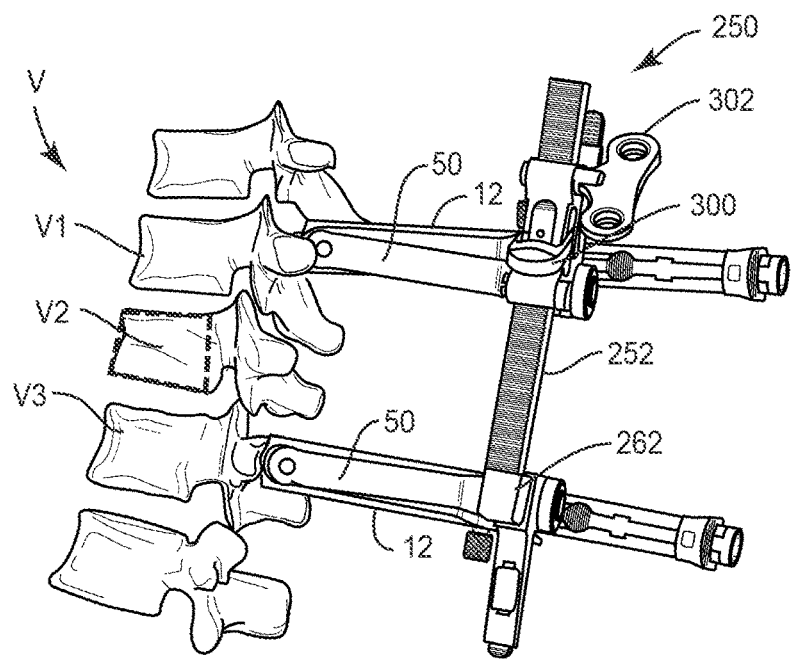
FIG. 15 is a side view of components of one embodiment of a surgical system in accordance with the principles of the present disclosure disposed with vertebrae.
Figure 16:
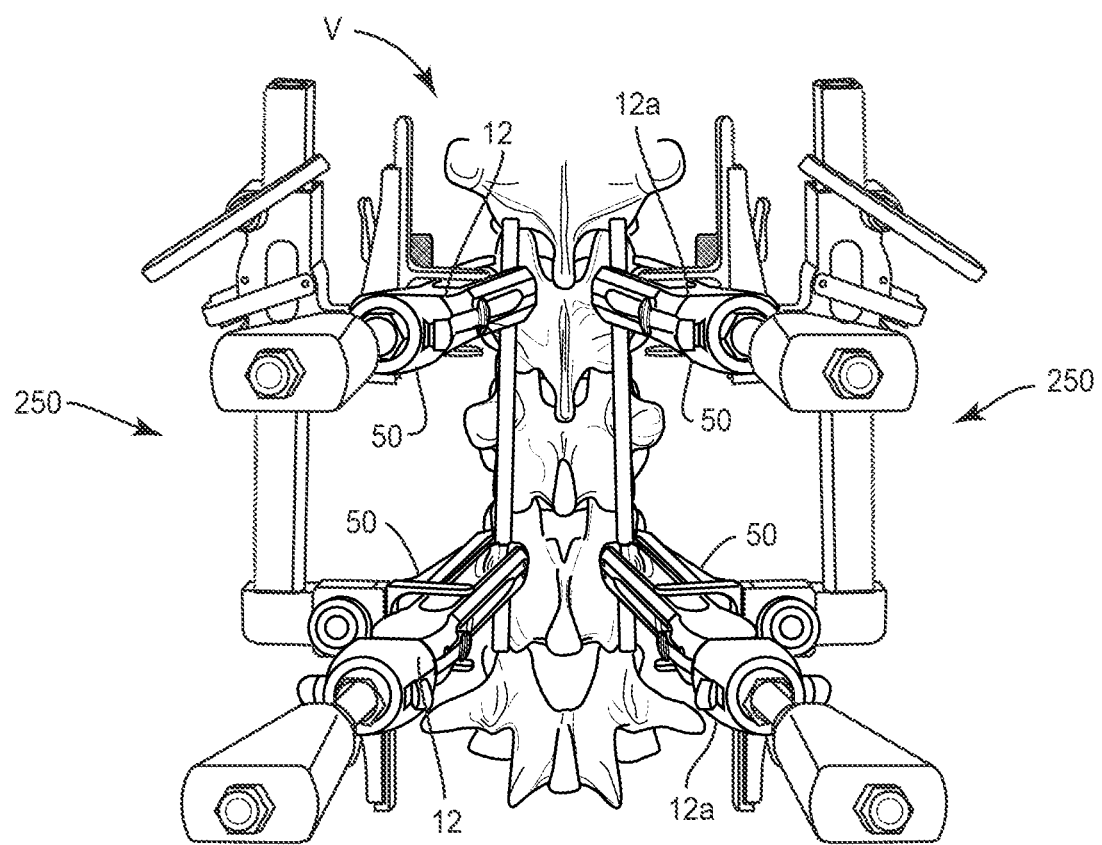
FIG. 16 is a plan view of components of one embodiment of a surgical system in accordance with the principles of the present disclosure disposed with vertebrae.
Figure 17:
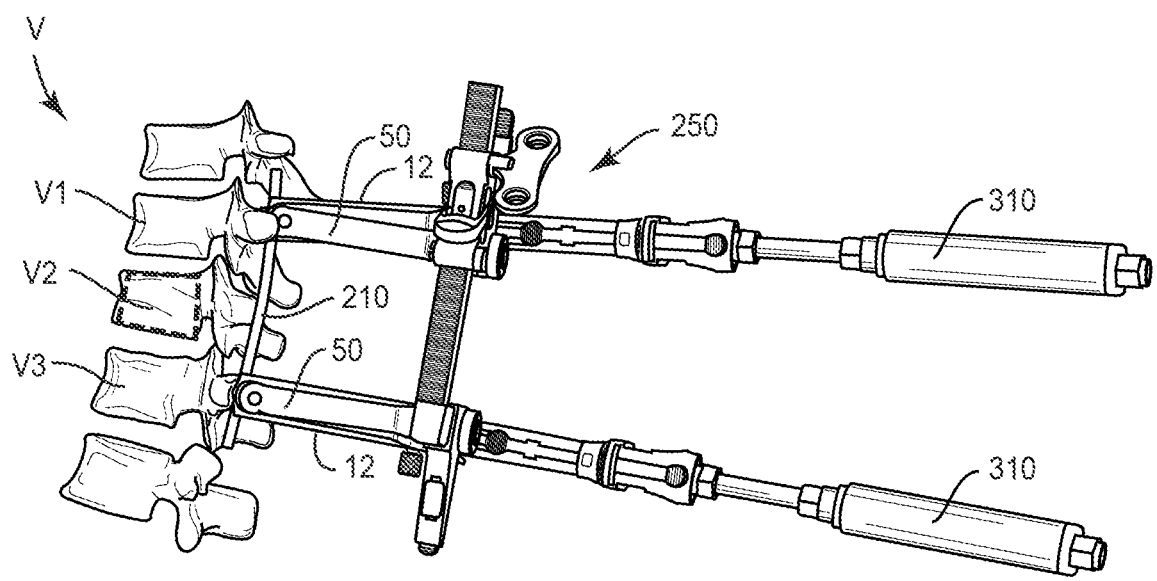
FIG. 17 is a side view of components of one embodiment of a surgical system in accordance with the principles of the present disclosure disposed with vertebrae.

Compressor/distractor 250 is connected with extenders 12, 12a to allow for distraction and/or compression of vertebrae V connected with extenders 12, 12a. For example, latch 300 is pivotable to the distraction position, as described herein, to allow translation of arm 282, in the direction shown by arrow A, and prevent translation of arm 282, in the direction shown by arrow B, relative to arm 262/rack 252, as shown in FIG. 13. As such, distraction of vertebrae V1, V3 connected with extenders 12, 12a can be performed. A key 302 is engageable with splines 260 to translate rack 252 for distraction. In some embodiments, keys 302 can simultaneously engage compressor/distractors 250 connected with vertebrae V on sides L, CL to perform parallel distraction of vertebrae V1, V3, as shown in FIG. 14.

Rod 210 is disposed within receivers 202 of FAS 200. A surgical instrument, such as, for example, a driver 310 is connected with set screws 212. Drivers 310 engage set screws 212 with rod 210 to fix rod 210 with FAS 200.

Figure 20:
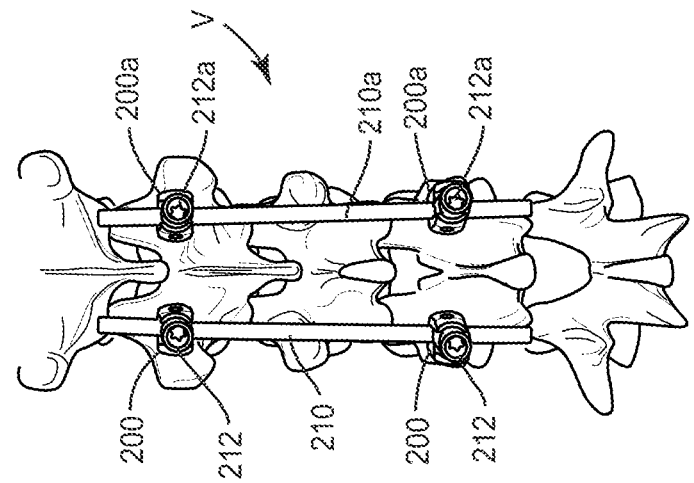
FIG. 20 is a side view of components of one embodiment of a surgical system in accordance with the principles of the present disclosure disposed with vertebrae.

Vertebrae V is aligned to a selected orientation for sagittal, coronal and/or axial correction, as shown in FIGS. 19 and 20.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In some embodiments, surgical system 10 includes one or a plurality of alternate surgical instruments, each configured for mating engagement in a quick release configuration with spinal constructs, as described herein. This configuration facilitates the interchangeability of the spinal constructs with the alternate surgical instruments. In some embodiments, surgical system 10 includes one or a plurality of alternate surgical instruments, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

Figure 22:
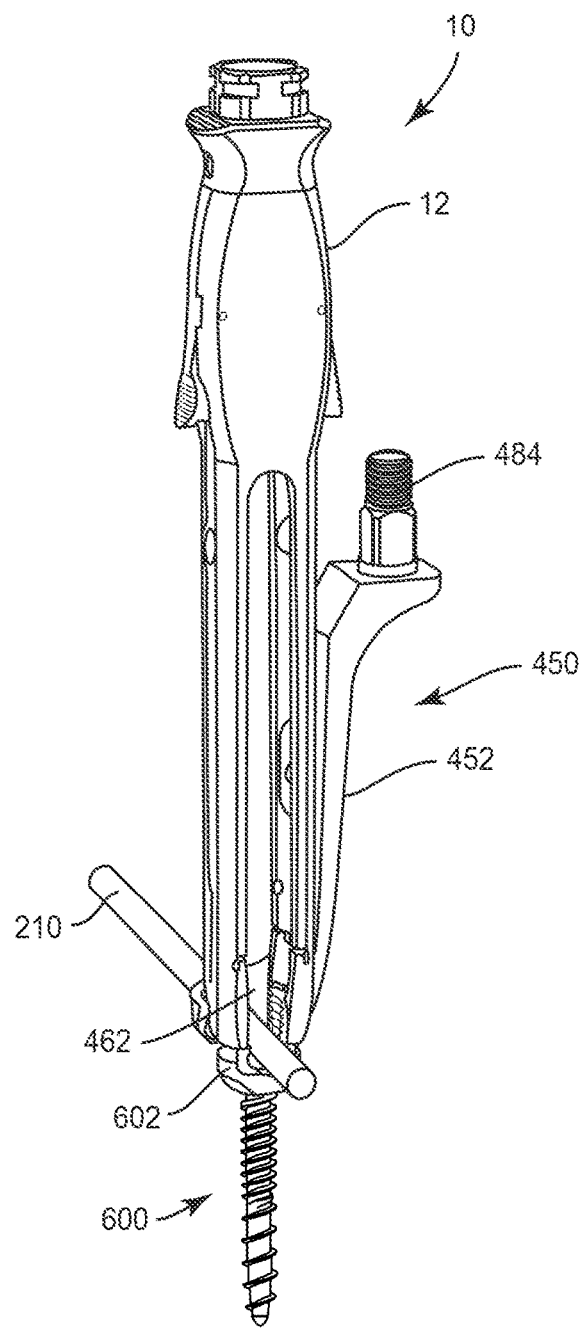
FIG. 22 is a perspective view of components of one embodiment of a surgical system in accordance with the principles of the present disclosure.
Figure 23:
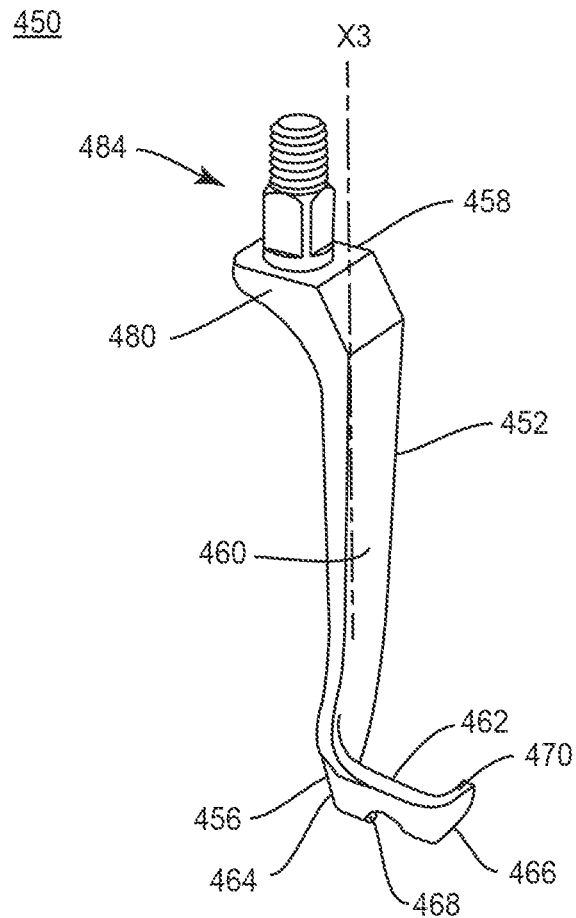
FIG. 23 is a perspective view of components of one embodiment of a surgical system in accordance with the principles of the present disclosure.
Figure 24:
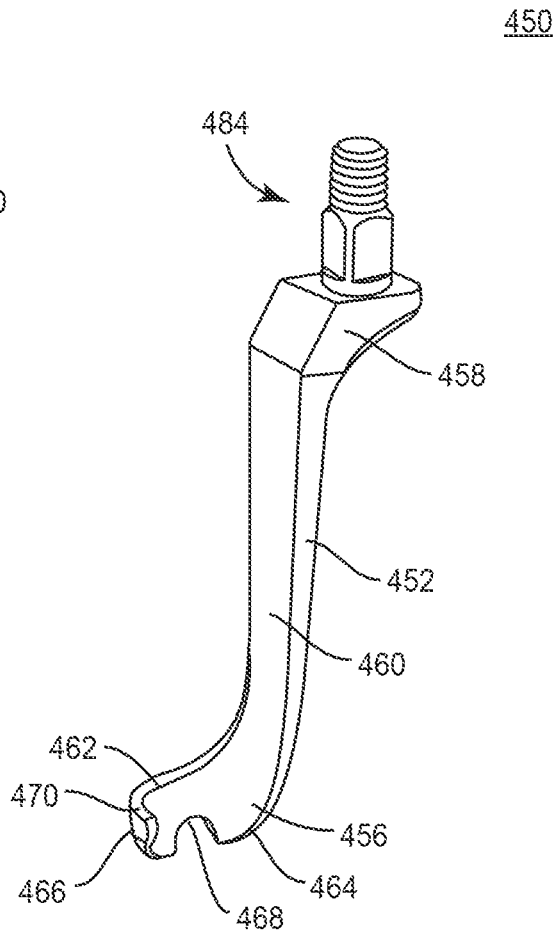
FIG. 24 is a perspective view of components of one embodiment of a surgical system in accordance with the principles of the present disclosure.
Figure 25:
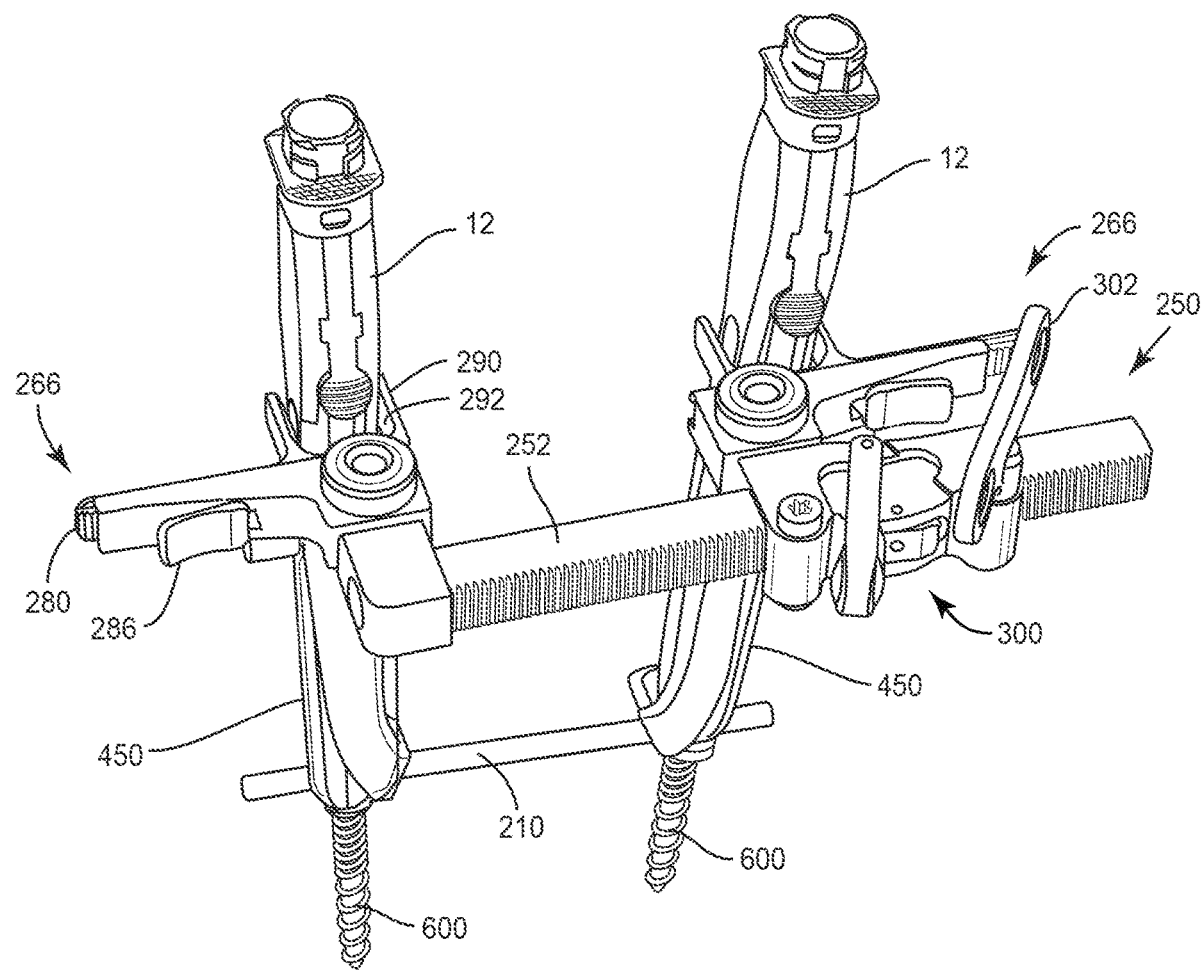
FIG. 25 is a perspective view of components of one embodiment of a surgical system in accordance with the principles of the present disclosure.

In one embodiment, as shown in FIGS. 21-41, surgical system 10, similar to the systems and methods described with regard to FIGS. 1-20, includes an adaptor 450, similar to adaptors 50, 550 described herein. Adaptor 450 includes a longitudinal member, such as, for example, a body 452. Body 452 extends along an axis X3 between an end 456 and an end 458, as shown in FIGS. 23 and 24. Body 452 is configured to extend along leg 14 and/or leg 18, as described herein. In some embodiments, all or only a portion of body 452 may include cross section configurations, such as, for example, oval, oblong, triangular, square, polygonal, irregular, uniform, non-uniform, offset, staggered, undulating, arcuate, variable and/or tapered.

Body 452 includes a surface 460. A transverse member, such as, for example, an arm 462 extends from surface 460. Arm 462 extends between an end 464 and an end 466. Arm 462 extends transverse to axis X3. In some embodiments, arm 462 may be variously oriented relative to axis X3, such as, for example, perpendicular, angular and/or offset. In some embodiments, arm 462 is monolithically formed with body 452. In some embodiments, all or only a portion of arm 462 may include cross section configurations, such as, for example, oval, oblong, triangular, square, polygonal, irregular, uniform, non-uniform, offset, staggered, undulating, arcuate, variable and/or tapered.

Figure 21:
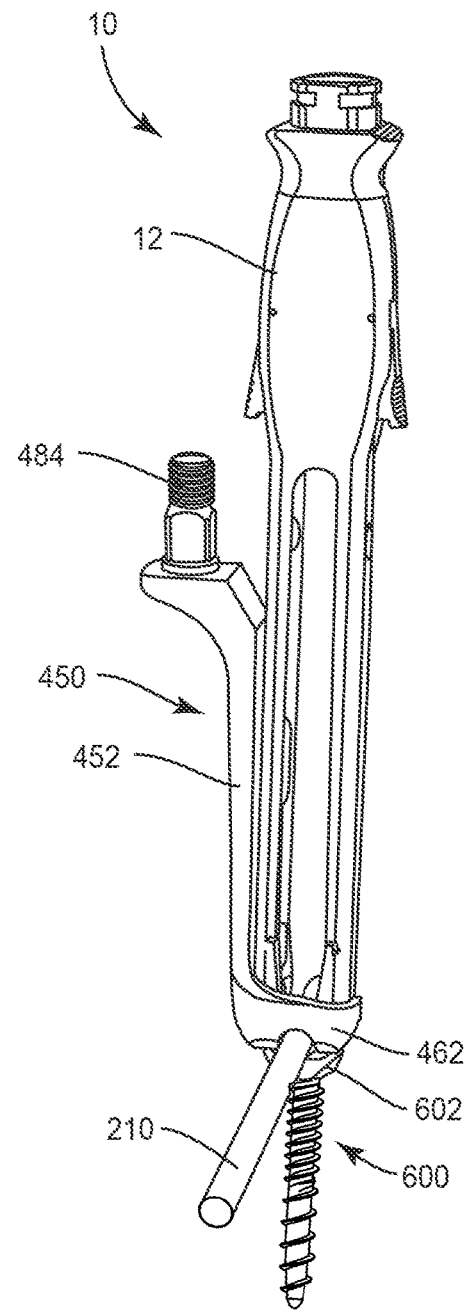
FIG. 21 is a perspective view of components of one embodiment of a surgical system in accordance with the principles of the present disclosure.

Arm 462 includes a surface that defines a recess 468 configured for engagement with spinal rod 210, as described herein. Recess 468 includes a concave portion for disposal of rod 210 such that arm 462 extends adjacent to rod 210, as shown in FIG. 21. Arm 462 includes a hook 470 disposed at end 466. A surface of hook 470 is configured to engage a portion of extenders 12. For example, body 452 extends along legs 14 and the surface of hook 470 engages leg 18 to facilitate connection of adaptor 450 with extenders 12, as shown in FIGS. 21 and 22. End 458 includes a projection 480 having a threaded lock surface 484, similar to surface 84 described herein.

Figure 28:
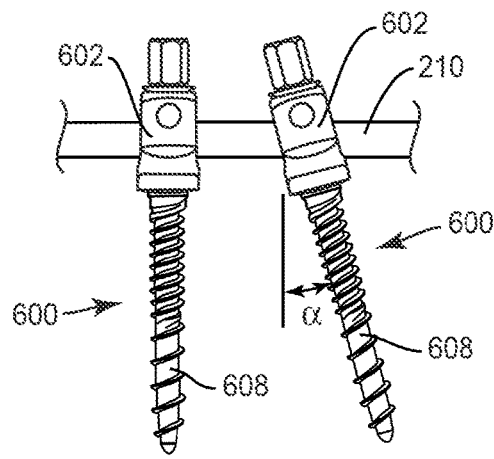
FIG. 28 is a side view of components of one embodiment of a surgical system in accordance with the principles of the present disclosure.
Figure 27:
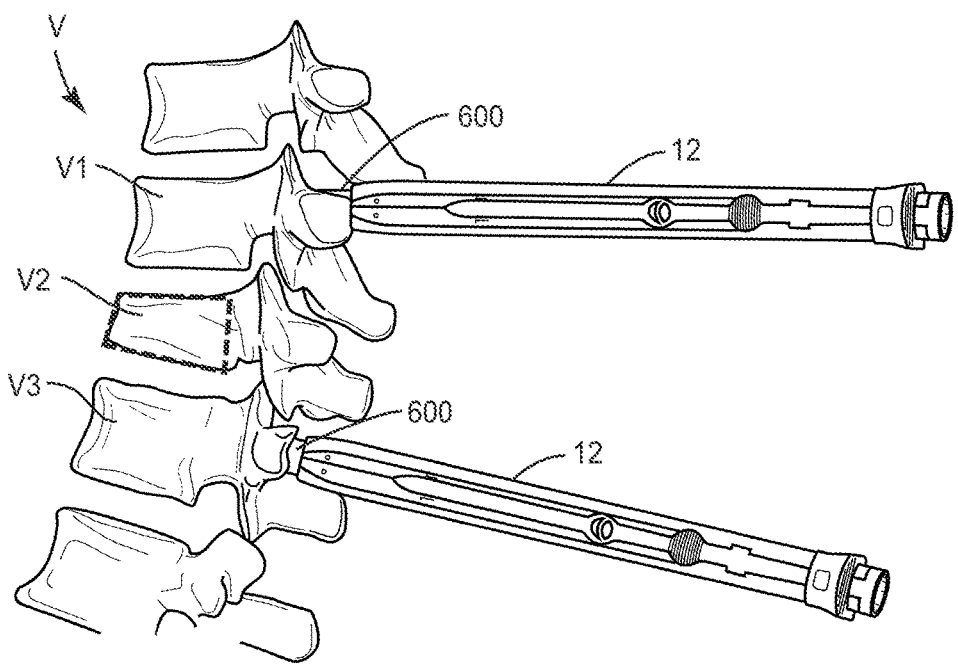
FIG. 27 is a side view of components of one embodiment of a surgical system in accordance with the principles of the present disclosure disposed with vertebrae.
Figure 29:
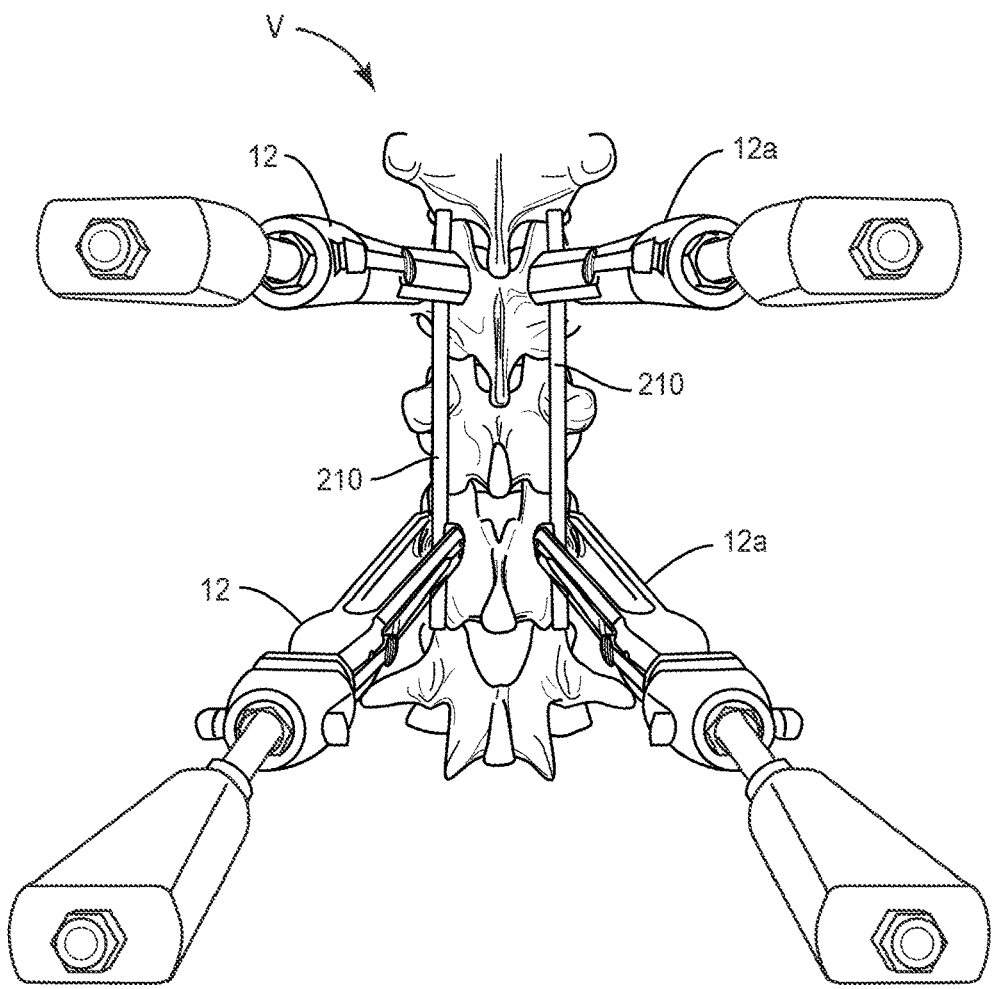
FIG. 29 is a plan view of components of one embodiment of a surgical system in accordance with the principles of the present disclosure disposed with vertebrae.
Figure 30:
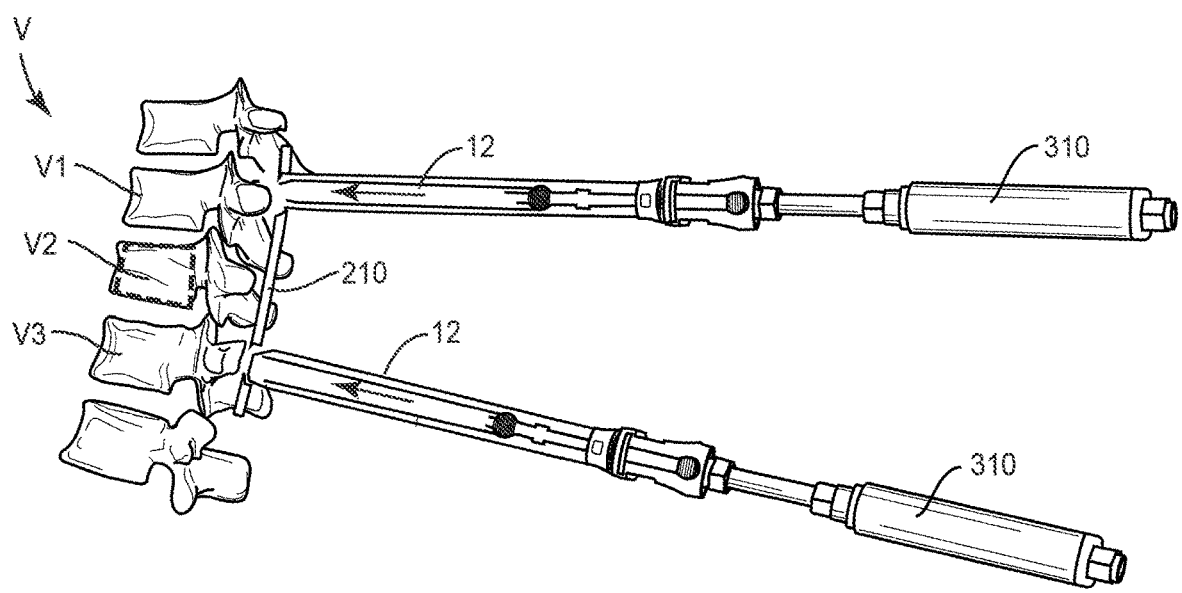
FIG. 30 is a side view of components of one embodiment of a surgical system in accordance with the principles of the present disclosure disposed with vertebrae.
Figure 31:
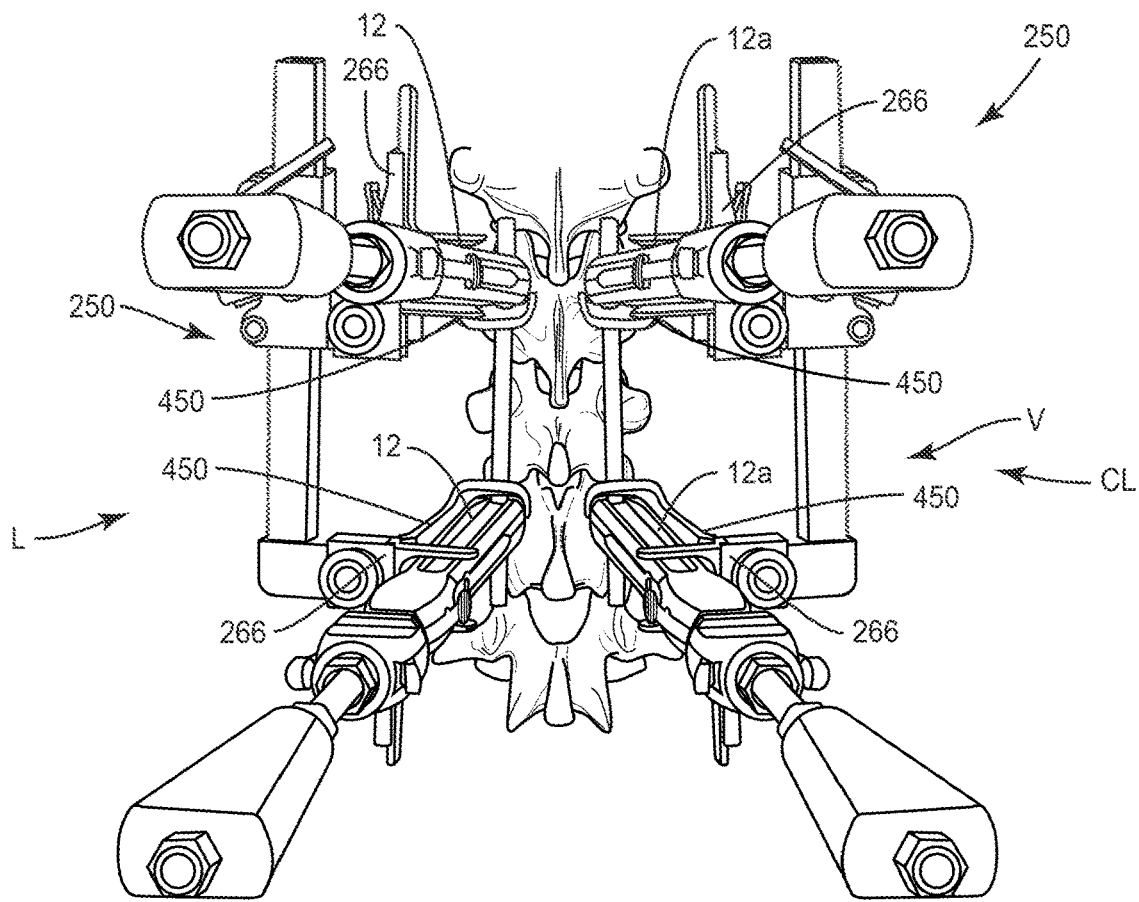
FIG. 31 is a plan view of components of one embodiment of a surgical system in accordance with the principles of the present disclosure disposed with vertebrae.

Surgical system 10 includes a SAS 600 having a receiver 602, as shown in FIG. 28. Receiver 602 is configured for engagement with extenders 12, as described herein and includes a shaft 608 configured for penetrating tissue. Receiver 602 includes a saddle (not shown) that is selectively translatable within receiver 602 in a sagittal plane to accommodate sagittal anatomical differences. The saddle receives and movably supports rod 210 such that rod 210 is movable within receiver 602 through an angular range.

Figure 39:
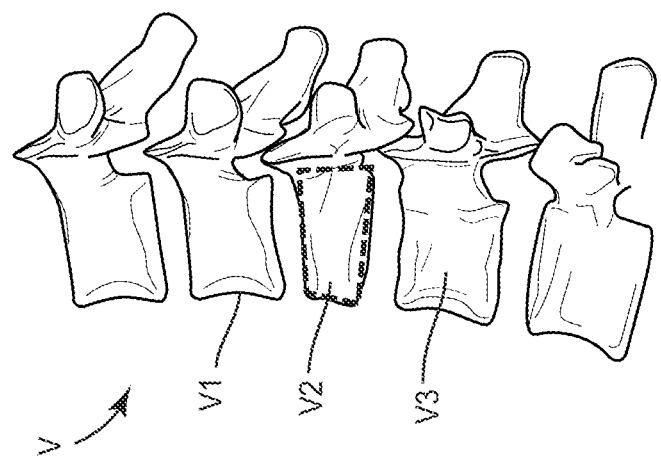
FIG. 39 is a side view of vertebrae.

In assembly, operation and use, surgical system 10, similar to the systems and methods described herein, is employed with a surgical procedure, for treatment of a spine of a patient including vertebrae V, as shown in FIGS. 25-41. Surgical system 10 is employed with a procedure for treatment of an applicable condition or injury of an affected section of a spinal column and adjacent areas within a body. For example, vertebrae V includes a vertebral level V1, a vertebral level V2 and a vertebral level V3, as shown in FIG. 39. Diseased and/or damaged vertebrae and intervertebral discs are disposed at vertebra V2 between vertebrae V1 and V3.

Figure 26:
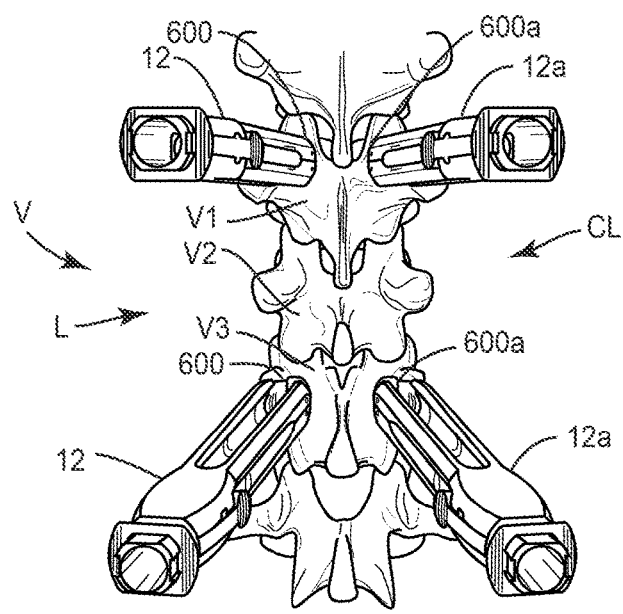
FIG. 26 is a plan view of components of one embodiment of a surgical system in accordance with the principles of the present disclosure disposed with vertebrae.

Pilot holes or the like are made in selected vertebrae V1 and V3 for receiving SAS 600, 600*a*. A driver (not shown) is disposed adjacent vertebrae V at the surgical site and is manipulated to drive, torque, insert or otherwise connect SAS 600, 600*a* with vertebrae V1 and V3. SAS 600, 600*a* are engaged with vertebrae V along a lateral side L and a contra-lateral CL side of vertebrae V, as shown in FIG. 26. Extenders 12 are engaged with SAS 600 and extenders 12*a* are engaged with SAS 600*a*.

Rod 210 is disposed within receivers 602 of SAS 600, as shown in FIGS. 28-32. The saddle receives and movably supports rod 210 such that rod 210 is movable within receiver 602 through an angular range α, as shown in FIG. 28. The saddle provides movement of rod 210 to facilitate sagittal accommodation of rod 210 such that SAS 600 provides angular accommodation in a transverse plane and a sagittal plane of vertebrae.

Figure 32:
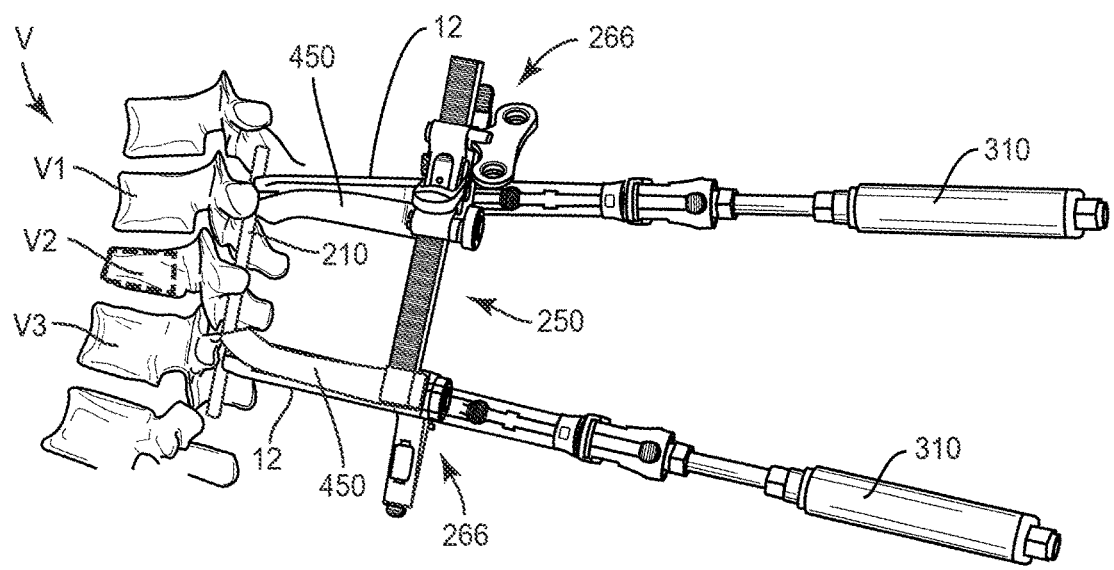
FIG. 32 is a side view of components of one embodiment of a surgical system in accordance with the principles of the present disclosure disposed with vertebrae.
Figure 33:
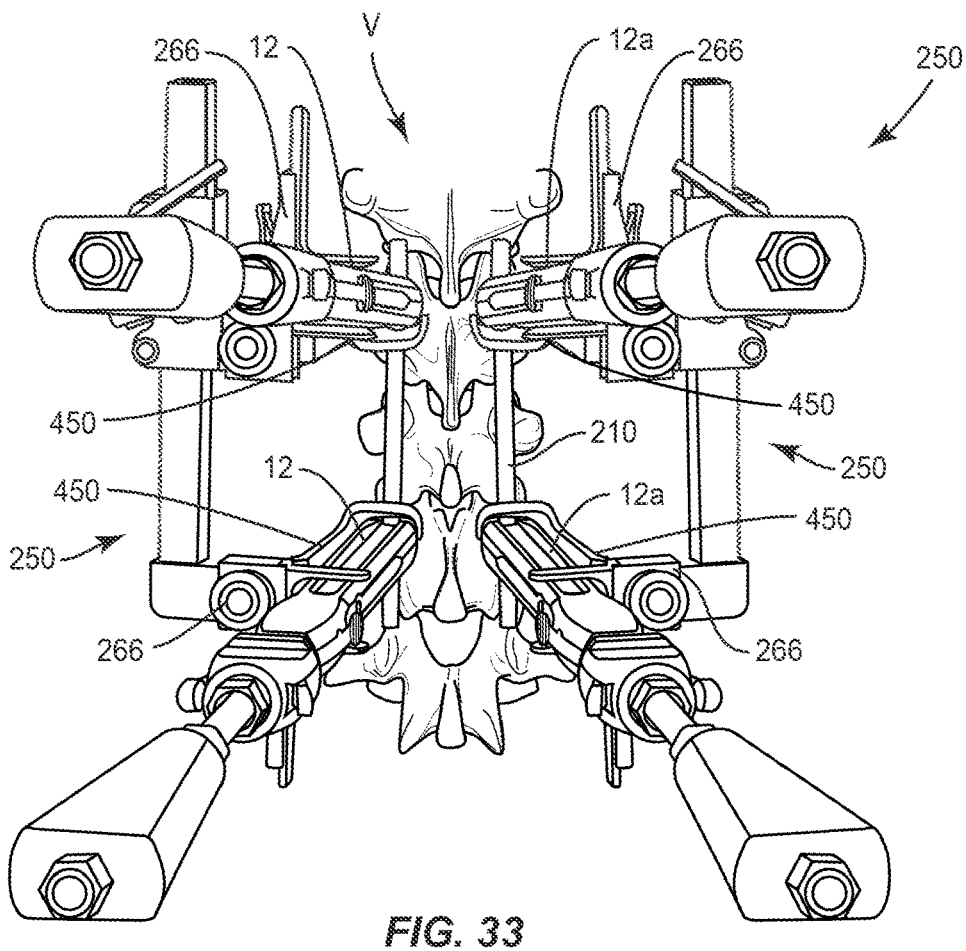
FIG. 33 is a plan view of components of one embodiment of a surgical system in accordance with the principles of the present disclosure disposed with vertebrae.
Figure 34:
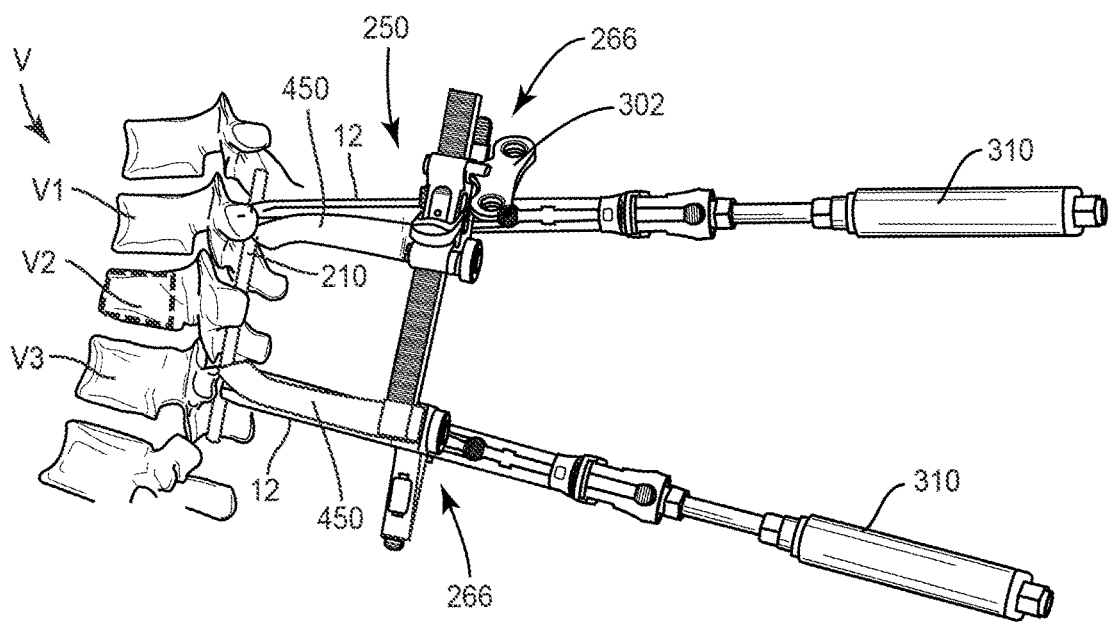
FIG. 34 is a side view of components of one embodiment of a surgical system in accordance with the principles of the present disclosure disposed with vertebrae.
Figure 35:
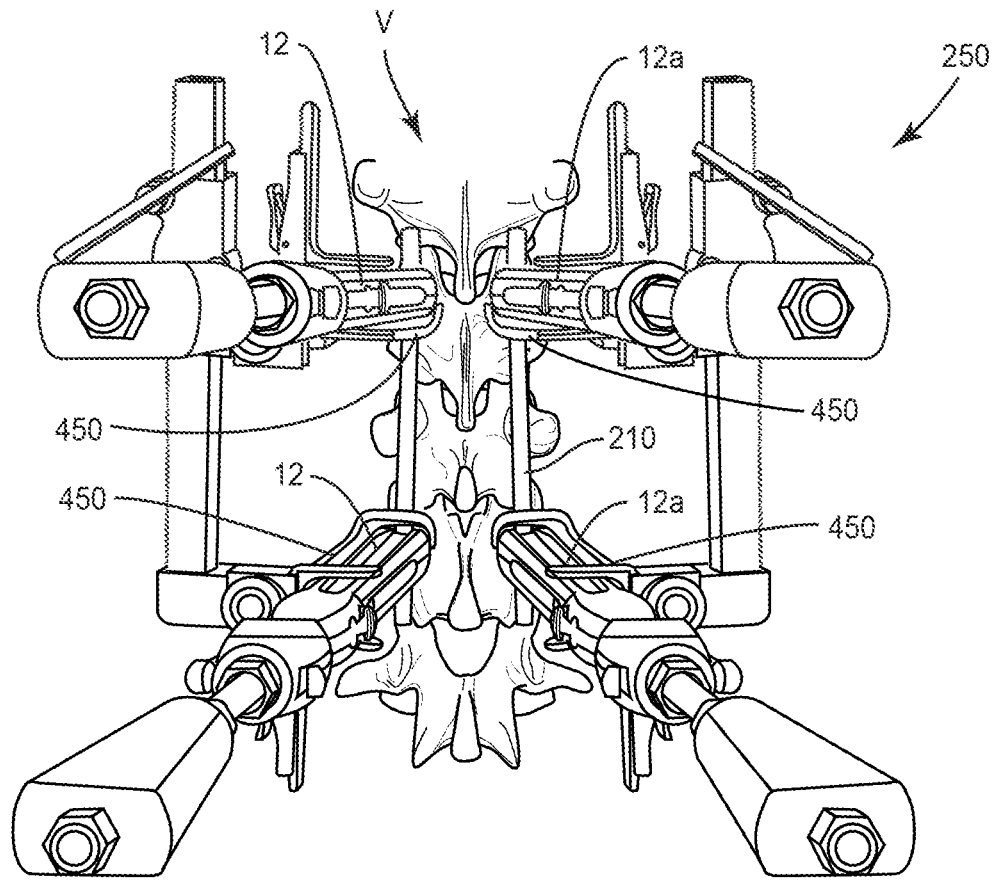
FIG. 35 is a plan view of components of one embodiment of a surgical system in accordance with the principles of the present disclosure disposed with vertebrae.
Figure 36:
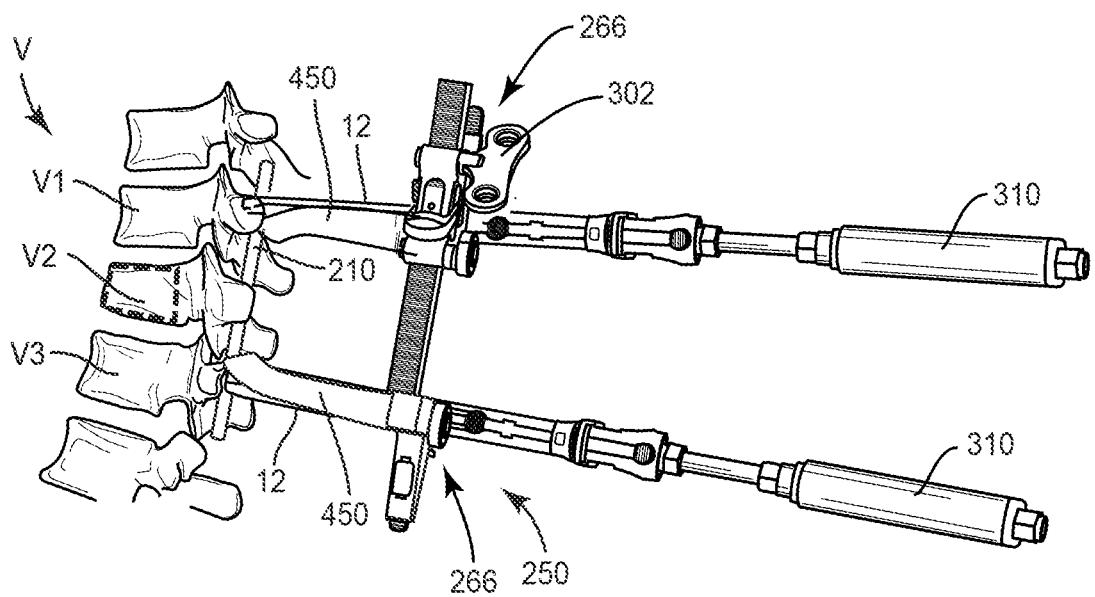
FIG. 36 is a side view of components of one embodiment of a surgical system in accordance with the principles of the present disclosure disposed with vertebrae.
Figure 37:
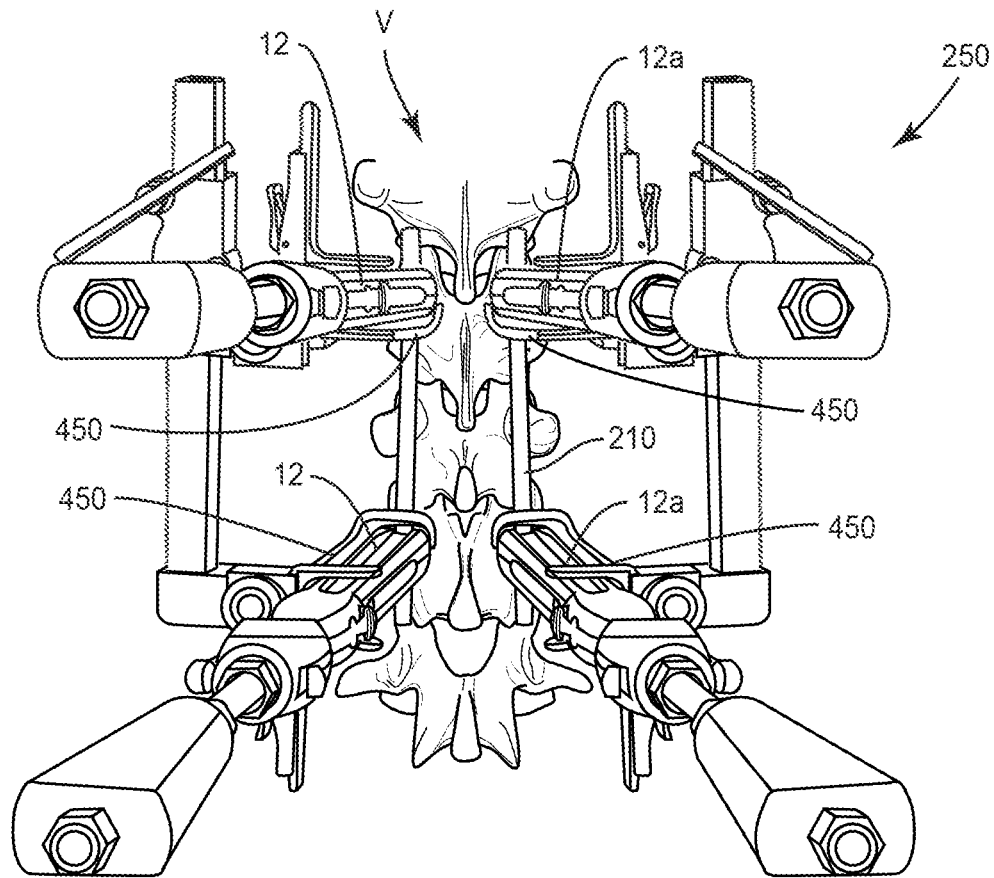
FIG. 37 is a plan view of components of one embodiment of a surgical system in accordance with the principles of the present disclosure disposed with vertebrae.
Figure 38:
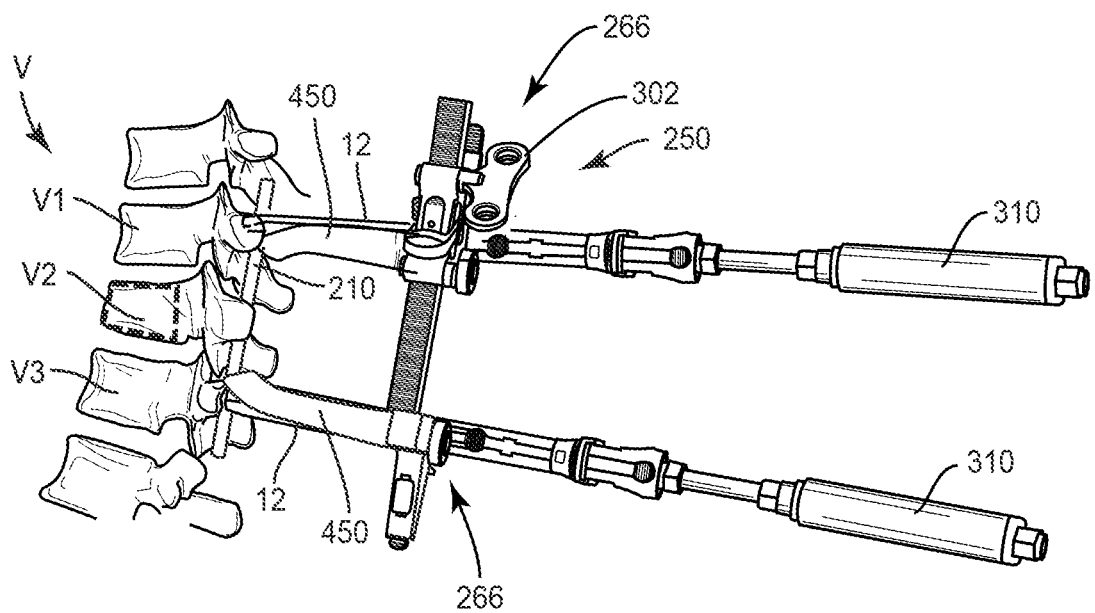
FIG. 38 is a side view of components of one embodiment of a surgical system in accordance with the principles of the present disclosure disposed with vertebrae.

Drivers 310 are connected with set screws 212 to provisionally fix rod 210 with SAS 600. In some embodiments, driver 310 may be engageable with rod 210 for reduction with SAS 600, 600*a*. Adaptors 450 are connected with extenders 12, 12*a*, as described herein. Rod 210 is provisionally disposed with recess 468 such that arm 462 is disposed adjacent rod 210, as shown in FIG. 32. A surface of hook 470 engages extenders 12, 12*a* to facilitate connection of adaptor 450 with extenders 12, 12*a*.

Drivers 310 loosen set screws 212 to release rods 210. The release of rod 210 allows for manipulation and reduction of rod 210. Compressor/distractor 250 and modules 266 are mounted with adaptors 450 via surface 484 and lock nut 274 for fixation therewith, as described with regard to FIGS. 1-20. Arms 290 of modules 266 capture extenders 12, 12*a*, as described herein. Modules 266 are fixed with extenders 12, 12*a*, to allow for angulation and/or correction of vertebrae V connected with extenders 12, 12*a*, as described with regard to FIGS. 1-20. Compressor/distractor 250 is connected with extenders 12, 12*a*, to allow for distraction and/or compression of vertebrae V connected with extenders 12, 12a, as described with regard to FIGS. 1-20.

Figure 41:
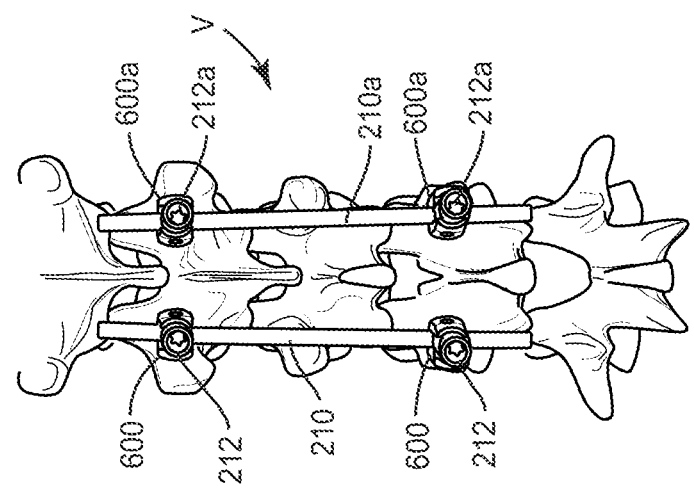
FIG. 41 is a side view of components of one embodiment of a surgical system in accordance with the principles of the present disclosure disposed with vertebrae.
Figure 40:
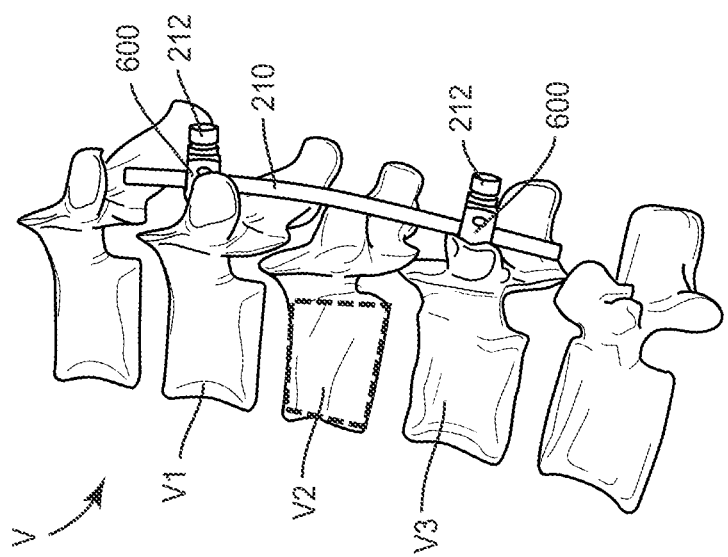
FIG. 40 is a side view of components of one embodiment of a surgical system in accordance with the principles of the present disclosure disposed with vertebrae.

Drivers 310 tighten set screws 212 and fix rod 210 with SAS 600. Vertebrae V is aligned to a selected orientation for correction, as shown in FIGS. 40 and 41.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

The invention claimed is:

1. A surgical system comprising:
    at least one implant support including a first implant support that is engageable with a receiver of a first fastener having a shaft fixed with vertebral tissue;
    at least one adaptor including a first adaptor extending longitudinally along and being engageable with the first implant support, the first adaptor comprising first and second extensions, distal ends of the extensions being joined together and opposite proximal ends of the extensions being spaced apart from one another, the first adaptor comprising an actuator extending through the proximal ends and configured to increase and decrease a distance between the proximal ends to capture the first implant support, the first adaptor being oriented to releasably engage a surgical instrument to distract and/or compress the vertebral tissue; and
    an angulation module connected to at least one of the first adaptor, the first implant support and the surgical instrument,
    wherein the angulation module includes spaced apart first and second arms configured to capture the first implant support, the second arm being fixed relative to the first arm.

2. A surgical system as recited in claim 1, wherein the angulation module is connected with the first implant support to rotate the first implant support and the vertebral tissue connected therewith.

3. A surgical system as recited in claim 1, wherein the angulation module engages the first implant support to fix the first implant support and the vertebral tissue connected therewith at a selected angular orientation relative to the surgical instrument.

4. A surgical system as recited in claim 1, wherein the angulation module includes a ratchet.

5. A surgical system as recited in claim 1, wherein the angulation module includes a ratchet that prevents movement in a first direction and a second direction.

6. A surgical system as recited in claim 1, further comprising a locking element for connecting the angulation module, the first adaptor, the first implant support and the surgical instrument.

7. A surgical system as recited in claim 1, further comprising a second implant support engageable with a receiver of a second fastener having a shaft fixed with the tissue, and a second adaptor extending longitudinally along and being engageable with the second implant support, the adaptors being oriented to releasably engage the surgical instrument to distract and/or compress the vertebral tissue.

8. A surgical system as recited in claim 1, wherein the surgical instrument includes a ratchet.

9. A surgical system as recited in claim 1, wherein the surgical instrument includes a ratchet that prevents movement in a first direction and a second direction.

10. A surgical system as recited in claim 1, wherein the first adaptor is adjustable to connect the first implant support with the surgical instrument.

11. A surgical system as recited in claim 1, wherein the first adaptor is connected with the first implant support adjacent the receiver of the first fastener and rotatably adjustable to connect the first implant support with the surgical instrument.

12. A surgical system as recited in claim 1, wherein the first adaptor is movable between a first orientation in which the proximal ends extend parallel relative to one another and a second orientation in which the proximal ends extend at a non-zero angle relative to one another.

13. A surgical system as recited in claim 1, wherein the first implant support includes first and second legs, the actuator being rotatable relative to the extensions to draw the extension to compress and capture the legs.

14. A surgical system as recited in claim 1, wherein the first adaptor is movable between an open orientation and a closed orientation, the distance being greater when the first adaptor is in the open orientation, the first adaptor being biased to the open orientation.

15. A surgical system as recited in claim 14, wherein rotation of the actuator overcomes a bias of the extensions to move the first adaptor from the open orientation to the closed orientation.

16. A surgical system comprising:
    at least one implant support including a first implant support that is engageable with a receiver of a first fastener having a shaft fixed with vertebral tissue;
    at least one adaptor including a first adaptor extending longitudinally along and being engageable with the first implant support, the first adaptor comprising first and second extensions, distal ends of the extensions being joined together and opposite proximal ends of the extensions being spaced apart from one another, the first adaptor comprising an actuator extending through the proximal ends and configured to increase and decrease a distance between the proximal ends to capture the first implant support, the first adaptor being oriented to releasably engage a surgical instrument to distract and/or compress the vertebral tissue; and
    an angulation module connected to at least one of the first adaptor, the first implant support and the surgical instrument,
    wherein the angulation module includes a ratchet and spaced apart first and second arms, the arms being configured to capture the first implant support, the second arm being fixed relative to the first arm.

17. A surgical system as recited in claim 16, wherein the ratchet prevents movement in a first direction and a second direction.

18. A surgical system comprising:
    at least one implant support including a first implant support that is engageable with a receiver of a first fastener having a shaft fixed with vertebral tissue;
    at least one adaptor including a first adaptor extending longitudinally along and being engageable with the first implant support, the first adaptor comprising first and second extensions, distal ends of the extensions being joined together and opposite proximal ends of the extensions being spaced apart from one another, the first adaptor comprising an actuator extending through the proximal ends and configured to increase and decrease a distance between the proximal ends to capture the first implant support, the first adaptor being oriented to releasably engage a surgical instrument to distract and/or compress the vertebral tissue;

an angulation module connected to at least one of the first adaptor, the first implant support and the surgical instrument, the angulation module including spaced apart first and second arms configured to capture the first implant support, the second arm being fixed relative to the first arm; and a locking element for connecting the angulation module, the first adaptor, the first implant support and the surgical instrument.

19. A surgical system as recited in claim 18, wherein the surgical instrument includes a ratchet.

\* \* \* \* \*